United States Patent [19]

Seiler et al.

[11] Patent Number: 5,041,157
[45] Date of Patent: Aug. 20, 1991

[54] 1,2,4-TRIAZOLO[1,5-A]PYRIDIMIDIN-2-YLSULFONYL-3-AMINOTHIOPHENE-2-CARBOXYLIC ESTERS AS ANTIDOTES FOR CERTAIN HERBICIDES

[75] Inventors: Alfred Seiler, Stein, Switzerland; Hans-Dieter Schneider, Weil am Rhein, Fed. Rep. of Germany; Dieter Dürr, Bottmingen, Switzerland

[73] Assignee: Ciba-Geigy Corporation, Ardsley, N.Y.

[21] Appl. No.: 461,602

[22] Filed: Jan. 5, 1990

[30] Foreign Application Priority Data

Jan. 11, 1989 [CH] Switzerland ............... 78/89
Nov. 6, 1989 [CH] Switzerland ............ 3987/89

[51] Int. Cl.$^5$ .................. A01N 43/90; C07D 471/02
[52] U.S. Cl. ......................................... 71/92; 47/57.6; 71/90; 71/93; 544/263; 548/263.8
[58] Field of Search ............... 71/92, 93, 90; 47/57.6; 544/263

[56] References Cited

U.S. PATENT DOCUMENTS

| | | | |
|---|---|---|---|
| 3,719,466 | 3/1973 | Ahle | 71/88 |
| 4,238,621 | 12/1980 | Levitt | 560/12 |
| 4,300,944 | 11/1981 | Bohner et al. | 71/94 |
| 4,420,325 | 12/1983 | Saners | 71/92 |
| 4,443,243 | 4/1984 | Fory et al. | 71/93 |
| 4,443,245 | 4/1984 | Meyer et al. | 71/93 |
| 4,478,635 | 10/1984 | Meyer et al. | 71/92 |
| 4,479,821 | 10/1984 | Schurter et al | 71/94 |
| 4,481,029 | 11/1984 | Levitt | 71/93 |
| 4,505,743 | 3/1985 | Schurter et al. | 71/94 |
| 4,537,619 | 8/1985 | Meyer et al. | 71/93 |
| 4,548,638 | 10/1985 | Hageman | 71/93 |
| 4,600,428 | 7/1986 | Szczepanski | 71/92 |
| 4,670,559 | 6/1987 | Szczepanski | 544/211 |
| 4,671,819 | 6/1987 | Meyer et al. | 71/93 |
| 4,713,109 | 12/1987 | Schurter et al. | 71/94 |
| 4,744,814 | 5/1988 | Kimura | 71/92 |
| 4,755,212 | 7/1988 | Kleschick et al. | 71/92 |
| 4,759,791 | 7/1988 | Fory | 71/91 |
| 4,780,125 | 10/1988 | Meyer et al. | 71/93 |
| 4,786,734 | 11/1988 | Hanagan | 546/293 |
| 4,954,164 | 9/1990 | Suzuki | 71/92 |

FOREIGN PATENT DOCUMENTS

| | | | |
|---|---|---|---|
| 0197895 | 10/1986 | European Pat. Off. | 544/463 |
| 0248968 | 12/1989 | European Pat. Off. | |
| 951652 | 3/1984 | United Kingdom | 544/463 |
| 2149792 | 6/1985 | United Kingdom | 71/92 |

OTHER PUBLICATIONS

Pallos et al., "Chemistry and Action of Herbicidal Antidotes", N.Y. Academic Press 1978 pp. 161–164.
The Pesticide Manual, 8th Ed. (1987), p. 6160, 6370, 7010, 9970, 10565.
R. Wegeler, Chemie der Pflanzenschutz-und Schadlingsbekampfungsmittel, vol. 5, Springer p. 194–195.

Primary Examiner—Donald G. Daus
Attorney, Agent, or Firm—Edward Mc C. Roberts

[57] ABSTRACT

The present invention relates to the novel use of antidotes of formula I

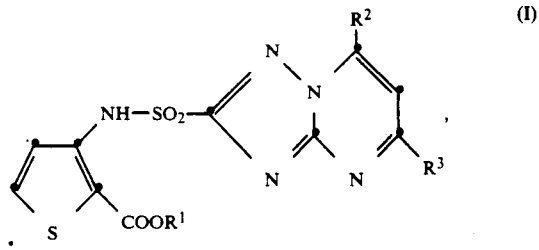

wherein $R^1$ is $C_1$–$C_6$alkyl or $C_3$–$C_6$cycloalkyl, and each of $R^2$ and $R^3$, independently of the other, is hydrogen, $C_1$–$C_3$alkyl, trifluoromethyl or cyclopropyl, with the proviso that only one of the symbols $R^2$ and $R^3$ may be hydrogen, for protecting cultivated plants from the phytotoxic action of herbicides. The invention relates also to novel compounds and the preparation thereof and to novel intermediates and the preparation thereof. The invention further relates to herbicidal composition that contain a combination of herbicide and antidote and to corresponding method of controlling weeds. Finally, the invention relates also to the seeds of cultivated plants protected by the treatment with the antidote.

21 Claims, No Drawings

1,2,4-TRIAZOLO[1,5-A]PYRIDIMIDIN-2-YLSULFONYL-3-AMINOTHIOPHENE-2-CARBOXYLIC ESTERS AS ANTIDOTES FOR CERTAIN HERBICIDES

The present invention relates to the novel use of antidotes of formula I for protecting cultivated plants from the phytotoxic action of herbicides. The invention relates also to novel compounds and the preparation thereof and to novel intermediates and the preparation thereof. The invention further relates to herbicidal compositions that contain a combination of herbicide and antidote and to methods of selectively controlling weeds by means of herbicide and antidote. Finally, the invention relates also to the seeds of cultivated plants protected by the treatment with the antidote.

It is known that herbicides belonging to the compound classes of sulfonylureas, haloacetanilides, aryloxyphenoxypropionic acid derivatives and N-benzoyl-N-phenylalanines, when employed in an effective concentration, sometimes also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. Damage to cultivated plants may also occur in the course of crop rotation if, following cultivated plants that are resistant to the herbicide used, other cultivated plants that have no resistance or only insufficient resistance to said herbicide are grown. The climatic conditions or the nature of the soil may be such that the concentration of herbicide recommended for normal conditions acts as an overdose. The quality of the seeds may also be a factor in the tolerance of the herbicide. To counteract the problem of insufficient selectivity of herbicides, various compounds have already been proposed which are able specifically to antagonise the harmful effect of the herbicide on the cultivated plant, i.e. to protect the cultivated plant without noticeably influencing the herbicidal action on the weeds to be controlled. However, it has been found that the proposed antidotes very often have species-specific activity with respect to both the cultivated plants and the herbicide and also, in some cases, contingent on the mode of application, i.e. a specific antidote is often suitable only for a specific cultivated plant and a few classes of herbicides.

U.S. Pat. No. 3,719,466 describes the protective treatment of seeds or seedlings of wheat and sorghum with certain oxamic acid esters and amides against attack by "ALACHLOR" (N-methoxymethyl-N-chloroacetyl-2,6-diethylaniline). U.S. Pat. No. 4,618,331 discloses benzoxazine derivatives having a protective action against the herbicidal action of haloacetanilides and sulfonylureas. For protection against sulfonylurea herbicides, EP-A-122 231 proposes as antidotes benzoyloxime ethers, and EP-A-147 365 phenylglyoxylic acid nitrile oxime, naphthalenedicarboxylic anhydride, a thiazolecarboxylic acid ester and also dichloroacetamides. According to DE-OS 2 402 983, maize plants can furthermore be effectively protected against damage caused by chloroacetanilides by applying to the soil as an antidote an N-disubstituted dichloroacetamide. Such compounds are also employed according to DE-OS 2 828 265 and 2 828 293 as antidotes to herbicidal acetanilides.

The use of thiophenecarboxylic acid esters as antidotes for protecting cultivated plants against sulfonylurea herbicides is described in EP-A-127 469.

It has now been found that, surprisingly, compounds of formula I

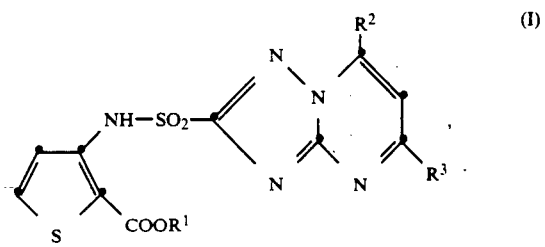

wherein $R^1$ is $C_1$-$C_6$alkyl or $C_3$-$C_6$cycloalkyl, and each of $R^2$ and $R^3$, independently of the other, is hydrogen, $C_1$-$C_3$alkyl, trifluoromethyl or cyclopropyl, with the proviso that only one of the symbols $R^2$ and $R^3$ may be hydrogen, are outstandingly suitable for protecting cultivated plants from the harmful effect of herbicides. The compounds of formula I are referred to hereinafter as "antidotes" or "safeners".

For protecting cultivated plants there are especially suitable a) antidotes of formula I wherein each of $R^2$ and $R^3$, independently of the other, is $C_1$-$C_3$alkyl or cyclopropyl, and $R^1$ is as defined for formula I;

b) antidotes of formula I wherein one of the symbols $R^2$ and $R^3$ is methyl and the other is cyclopropyl, and $R^1$ is as defined for formula I;

c) antidotes of formula I wherein $R^1$ is methyl and $R^2$ and $R^3$ are as defined for formula I;

d) antidotes of formula I wherein $R^1$ is $C_1$-$C_3$alkyl and each of $R^2$ and $R^3$, independently of the other, is hydrogen, methyl or cyclopropyl, with the proviso that only one of the symbols $R^2$ and $R^3$ may be hydrogen, and especially the antidote [N-(5,7-dimethyl-1,2,4-triazolo[1,5-a]pyrimidin-2-yl-sulfonyl)-3-aminothienyl-2]-carboxylic acid methyl ester of formula Ia

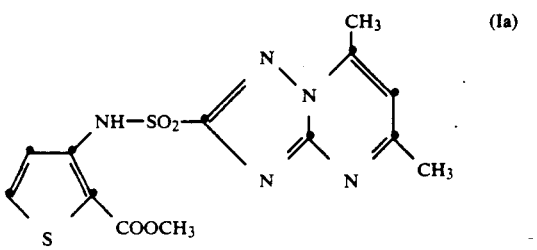

The compound of formula Ia is known from GB 2 149 792.

The invention relates also to novel compounds of formula I'

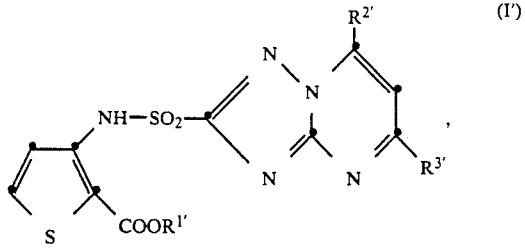

which fall within the scope of formula I and wherein $R^{1'}$ is $C_1$–$C_6$alkyl or $C_3$–$C_6$cycloalkyl, and each of $R^{2'}$ and $R^{3'}$, independently of the other, is hydrogen, $C_1$–$C_3$alkyl, trifluoromethyl or cyclopropyl, with the proviso that at least one of the symbols $R^{2'}$ and $R^{3'}$ is cyclopropyl, to the preparation of these compounds and to intermediates used for their preparation.

Of the compounds of formula I', there are especially worthy of mention those wherein a) one of the symbols $R^{2'}$ and $R^{3'}$ is cyclopropyl and the other is methyl, and $R^{1'}$ is as defined for formula I';

b) $R^{1'}$ is methyl and $R^{2'}$ and $R^{3'}$ are as defined for formula I; and c) $R^{1'}$ is methyl and one of the symbols $R^{2'}$ and $R^{3'}$ is cyclopropyl and the other is methyl.

Special prominence should be given to N-(7-cyclopropyl-5-methyl-1,2,4-triazolo[1,5-a]pyrimidin-2-ylsulfonyl)-3-aminothiophene-2-carboxylic acid methyl ester.

Depending on the end use, a safener or an antidote of the formula I can be used for pretreating seeds of the cultivated plant (dressing of the seeds or seedlings) or it can be added to the soil before or after sowing. However, it can also be applied pre- or post-emergence by itself alone or together with the herbicide. The treatment of the plant or seeds with the antidote can therefore in principle be carried out irrespective of the time of application of the herbicide. It can, however, also be carried out by simultaneous application of herbicide and safener (tank mixture). The pre-emergence treatment includes both treatment of the crop area before sowing (ppi=pre-plant incorporation) and treatment of the crop areas after sowing but before emergence of the plants.

The rates of application of the safener with respect to the herbicide depend largely on the mode of application. Where a field treatment is carried out, either simultaneously as tank mixture or with separate application of herbicide and safener, the ratio of safener to herbicide is in the range from 1:100 to 100:1. Full protective action is usually obtained at a ratio of safener to herbicide of 10:1 to 1:10. When dressing seeds and taking similar specific protective measures, however, much lower amounts of safener are required compared with the amount of herbicide later employed per hectare of crop area. For seed dressing, 0.01 to 6.0 g of safener per kg of seeds are normally required. Full protection is usually obtained with 0.1 to 2.0 g of safener per kg of seeds. If it is desired to apply the safener shortly before sowing by seed soaking, advantageously safener solutions which contain the active ingredient in a concentration of 1 to 10,000 ppm are used. Full protective action will normally be obtained with safener concentrations of 100 to 1000 ppm.

As a rule there is a substantial interval of time between protective measures, especially in the case of seed dressing and treatment of seedlings with a safener of formula I, and the possible later field treatment with herbicides. Accordingly, the invention relates also to plant protection compositions which consist of a safener of formula I' and one or more adjuvants, carriers or adjuvants/carriers. The invention further relates to herbicidal compositions which contain a compound of formula I as safener and a herbicide from whose effects the cultivated plant is to be protected, where appropriate together with adjuvants, carriers or adjuvants/carriers. The invention also relates to the propagation material of cultivated plants that has been pretreated with an active ingredient of formula I, such as seeds, seedlings or cuttings. The active ingredients of formula I are especially suitable for treating the seeds of soybeans and cereals. The term "cereals" within the scope of the present invention includes all species of cereal, especially wheat, rye, barley, oats, rice, sorghum and maize.

Cultivated plants within the scope of the present invention are plants that can be harvested and that are grown for that purpose, especially those plants which are used for human nutrition, such as especially soybeans and cereals.

Outstanding protective action against sulfonylurea herbicides, N-benzoyl-N-phenylalanine herbicides, aryloxyphenoxypropionic acid herbicides and chloroacetanilide herbicides is observed when antidotes of formula I are used especially in wheat, rye, barley, oats and rice. Numerous sulfonylurea herbicides whose harmful effect on cultivated plants can be reduced or eliminated by compounds of formula I have recently become known. Of the many publications disclosing herbicidally active sulfonylurea derivatives there may be mentioned by way of example U.S. Pat. Nos. 4,127,405 and 4,238,621 4,481,029, 4,432,245; 4,537,619, 4,420,325, 4,443,243, 4,478,635, 4,954,164, 4,780,125, 4,670,559; 4,671,819, 4,548,638, 4,744,814, 4,759,791 and 4,786,734.

Typical representatives of herbicidal sulfonylurea derivatives whose harmful effect on cultivated plants can be reduced or eliminated by antidotes of formula I are encompassed by formula II

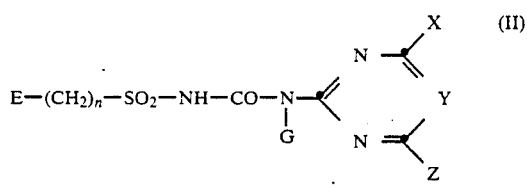

wherein E is one of the structural elements

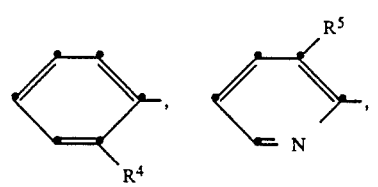

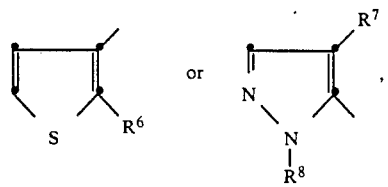

n is the number 0 or 1, G is hydrogen or methyl, X is methoxy, ethoxy, difluoromethoxy, methyl or chlorine, Y is CH or N, Z is methoxy, methyl, difluoromethoxy, cyclopropyl or methylamino, $R^4$ is $C_2$–$C_5$alkoxyalkoxy, $C_1$–$C_4$haloalkoxy, $C_1$–$C_4$haloalkylthio, $C_2$–$C_4$haloalkenyl, chlorine or $C_1$–$C_4$alkoxycarbonyl, $R^5$ is trifluoromethyl or di($C_1$–$C_4$alkyl)carbamoyl, $R^6$ is $C_1$–$C_4$alkoxycarbonyl, $R^7$ is $C_1$–$C_4$alkoxycarbonyl, and $R^8$ is $C_1$–$C_4$alkyl.

The following individual herbicidally active substances fall within the scope of formula II: N-(3-trifluoromethylpyridin-2-ylsulfonyl)-N'-(4,6-dimethoxypyrimidin-2-yl)-urea, N-(3-dimethylcarbamoylpyridin-2-ylsulfonyl)-N'-(4,6-dimethoxypyrimidin-2-yl)-urea, N-(1-methyl-4-ethoxycarbonylpyrazol-5-ylsulfonyl)-N'-(4,6-dimethoxypyrimidin-2-yl)-urea, N-(2-methoxycarbonylthien-3-ylsulfonyl)-N'-(4-methoxy-6-methyl-1,3,5-triazin-2-yl)-urea, N-(2-methoxycarbonylbenzylsulfonyl)-N'-(4,6-dimethoxypyrimidin-2-yl)-urea, N-(2-methoxycarbonylphenylsulfonyl)-N'-(4,6-bis-difluoromethoxypyrimidin-2-yl)-urea, N-(2-methoxycarbonylphenylsulfonyl)-N'-(4-ethoxy-6-methylamino-1,3,5-triazin-2-yl)-urea, N-(2-methoxycarbonylphenylsulfonyl)-N'-(4-methoxy-6-methyl-1,3,5-triazin-2-yl)-urea, N-(2-ethoxycarbonylphenylsulfonyl)-N'-(4-chloro-6-methoxypyrimidin-2-yl)-urea, N-(2-methoxycarbonylphenylsulfonyl)-N'-(4-methoxy-6-methyl-1,3,5-triazin-2-yl)-N'-methylurea, N-(2-methoxycarbonylphenylsulfonyl)-N'-(4,6-dimethoxypyrimidin-2-yl)-urea, N-(2-chlorophenylsulfonyl)-N'-(4-methoxy-6-methyl-1,3,5-triazin-2-yl)-urea, N-[2-(2-chloroethoxy)-phenylsulfonyl]-N'-(4-methoxy-6-methyl-1,3,5-triazin-2-yl)-urea and special prominence should be given to N-[2-(2-methoxyethoxy)-phenylsulfonyl]-N'-(4,6-dimethoxy-1,3,5-triazin-2-yl)-urea.

Numerous chloroacetanilides whose harmful effect on cultivated plants can be eliminated by compounds of formula I are also already known. Such chloroacetanilides can be described by the following general formula III:

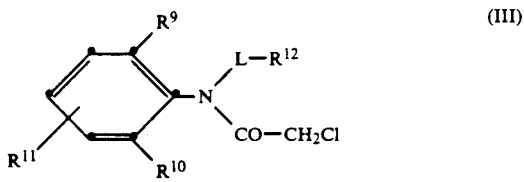

wherein L is a $C_1$–$C_5$alkylene bridge, especially a $C_1$–$C_4$alkylene bridge, each of $R^9$, $R^{10}$ and $R^{11}$, independently of the others, is hydrogen, halogen, $C_1$–$C_4$alkyl, $C_1$–$C_4$alkoxy, $C_1$–$C_4$haloalkyl, $C_2$–$C_5$alkoxyalkyl or $C_2$–$C_5$alkylthioalkyl, and $R^{12}$ is hydrogen, $C_1$–$C_4$alkoxy, —COOH, $C_1$–$C_4$alkoxycarbonyl, —CONH$_2$, $C_1$–$C_4$alkylcarbamoyl, di—$C_1$–$C_4$alkylcarbamoyl, cyano, $C_1$–$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl or unsubstituted or substituted tetrahydrofuryl, or the structural element —L—$R^{12}$ is a $C_1$–$C_4$alkylene bridge substituted by two $C_1$–$C_3$alkoxy groups or is 5-methyl-1,3,4-oxadiazol-2-yl.

The alkylene bridge L may be straight-chained or branched.

Preferred chloroacetanilides of formula III are those wherein L is a $C_1$–$C_4$alkylene bridge, each of $R^9$, $R^{10}$ and $R^{11}$, independently of the others, is hydrogen, halogen, $C_1$–$C_4$alkyl, $C_1$–$C_4$alkoxy, $C_1$–$C_4$haloalkyl, $C_2$–$C_5$alkoxyalkyl or $C_2$–$C_5$alkylthioalkyl, and $R^{12}$ is $C_1$–$C_4$alkoxy, —COOH, $C_1$–$C_4$alkoxycarbonyl, —CONH$_2$, $C_1$–$C_4$alkylcarbamoyl, di-$C_1$–$C_4$alkylcarbamoyl, cyano or $C_1$–$C_4$alkylcarbonyl.

The following herbicidal chloroacetanilide derivatives especially fall within the scope of formula III: N-ethoxymethyl-N-chloroacetyl-2-ethyl-6-methylaniline, N-chloroacetyl-N-methoxymethyl-2,6-diethylaniline, N-chloroacetyl-N-(2-methoxyethyl)-2,6-dimethylaniline, N-chloroacetyl-N-(2-n-propoxyethyl)-2,6-dimethylaniline, N-chloroacetyl-N-(2-isopropoxyethyl)-2,6-dimethylaniline, N-chloroacetyl-N-(2-methoxyethyl)-2-ethyl-6-methylaniline, N-chloroacetyl-N-(2-methoxyethyl)-2,6-diethylaniline, N-(2-ethoxyethyl)-N-chloroacetyl-2-ethyl-6-methylaniline, N-chloroacetyl-N-(2-methoxy-1-methylethyl)-2-methylaniline, N-chloroacetyl-N-(2-methoxy-1-methylethyl)-2,6-dimethylaniline, N-chloroacetyl-N-(2-methoxy-1-methylethyl)-2,6-diethylaniline, N-chloroacetyl-N-(2-methoxy-1-methylethyl)-2-ethyl-6-methylaniline, N-(2-ethoxyethyl)-N-chloroacetyl-2,6-diethylaniline, N-chloroacetyl-N-(2-n-propoxyethyl)-2-ethyl-6-methylaniline, N-chloroacetyl-N-(2-n-propoxyethyl)-2,6-diethylaniline, N-chloroacetyl-N-(2-isopropoxyethyl)-2-ethyl-6-methylaniline, N-ethoxycarbonylmethyl-N-chloroacetyl-2,6-dimethylaniline, N-ethoxycarbonylmethyl-N-chloroacetyl-2,6-diethylaniline, N-chloroacetyl-N-methoxycarbonylmethyl-2,6-dimethylaniline, N-chloroacetyl-N-(2,2-diethoxyethyl)-2,6-dimethylaniline, N-chloroacetyl-N-(2-methoxy-1-methylethyl)-2,3-dimethylaniline, N-(2-ethoxyethyl)-N-chloroacetyl-2-methylaniline, N-chloroacetyl-N-(2-methoxyethyl)-2-methylaniline, N-chloroacetyl-N-(2-methoxy-2-methylethyl)-2,6-dimethylaniline, N-(2-ethoxy-2-methylethyl)-N-chloroacetyl-2-ethyl-6-methylaniline, N-chloroacetyl-N-(1-ethyl-11-methoxyethyl)-2,6-dimethylaniline, N-chloroacetyl-N-(2-methoxyethyl)-2-methoxy-6-methylaniline, N-n-butoxymethyl-N-chloroacetyl-2-tert.-butylaniline, N-(2-ethoxyethyl-2-methylethyl)-N-chloroacetyl-2,6-dimethylaniline, N-chloroacetyl-N-(2-methoxyethyl)-2-chloro-6-methylaniline, N-(2-ethoxyethyl)-N-chloroacetyl-2-chloro-6-methylaniline, N-(2-ethoxyethyl)-N-chloroacetyl-2,3,6-trimethylaniline, N-chloroacetyl-N-(2-methoxyethyl)-2,3,6-trimethylaniline, N-chloroacetyl-N-cyanomethyl-2,6-dimethylaniline, N-chloroacetyl-N-(1,3-dioxolan-2-ylmethyl)-2,6-dimethylaniline, N-chloroacetyl-N-(1,3-dioxolan-2-ylmethyl)-2-ethyl-6-methylaniline, N-chloroacetyl-N-(1,3-dioxan-2-ylmethyl)-2-ethyl-6-methylaniline, N-chloroacetyl-N-(2-furylmethyl)-2,6-dimethylaniline, N-chloroacetyl-N-(2-furylmethyl)-2-ethyl-6-methylaniline, N-chloroacetyl-N-(2-tetrahydrofurylmethyl)-2,6-dimethylaniline, N-chloroacetyl-N-(N,N-dimethylcarbamoylmethyl)-2,6-dimethylaniline, N-(n-butoxymethyl)-N-chloroacetyl-2,6-diethylaniline, N-(2-n-butoxyethyl)-N-chloroacetyl-2,6-diethylaniline, N-chloroacetyl-N-(2-methoxy-1,2-dimethylethyl)-2,6-dimethylaniline, N-chloroacetyl-N-isopropyl-2,3-dimethylaniline, N-chloroacetyl-N-isopropyl-2-chloroaniline, N-chloroacetyl-N-(1H-pyrazol-1-ylmethyl)-2,6-dimethylaniline, N-chloroacetyl-N-(1H-pyrazol-1-ylmethyl)-2-ethyl-6-methylaniline, N- chloroacetyl-N-(1H-1,2,4-triazol-1-ylmethyl)-2,6-dimethylaniline, N-chloroacetyl-N-(1H-1,2,4-triazol-1-ylmethyl)-2,6-diethylaniline, N-benzoylmethyl-N-chloroacetyl-2,6-diethylaniline, N-benzoylmethyl-N-chloroacetyl-2-ethyl-6-methylaniline, N-chloroacetyl-N-(5-methyl-1,3,4-oxadiazol-2-yl)-2,6-diethylaniline, N-chloroacetyl-N-(5-methyl-1,3,4-oxadiazol-2-yl)-2-ethyl-6-methylaniline, N-chloroacetyl-N-(5-methyl-1,3,4-oxadiazol-b 2-yl)-2-tert.-butylaniline, N-chloroacetyl-N-(4-chlorobenzoylmethyl)-2,6-dimethylaniline and N-chloroacetyl-N-(4-methyl-5-methylthio-1,2,4-triazol-3-ylmethyl)-2,6-diethylaniline.

Numerous aryloxyphenoxypropionic acid herbicides whose harmful effect on cultivated plants can be reduced or eliminated by antidotes of formula I are known. Such aryloxyphenoxypropionic acid derivatives can be described by the following general formula IV:

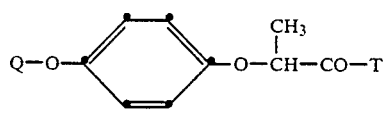

wherein Q is a radical

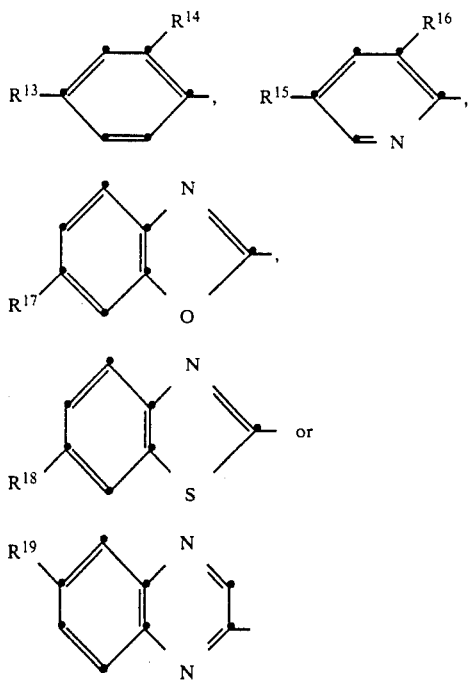

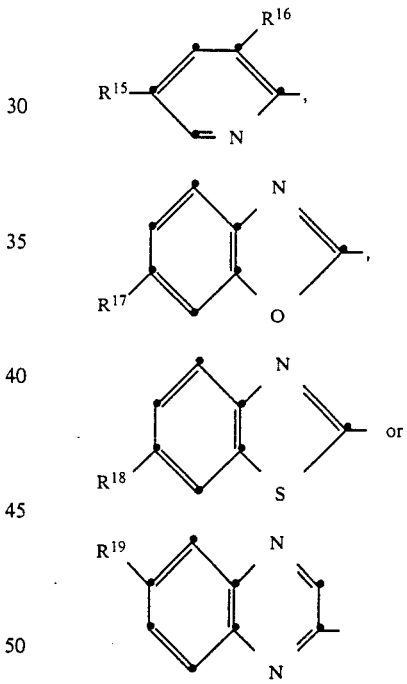

and T is $-NR^{20}R^{21}$, $-N(CN)R^{22}$, $-OR^{23}$, $SR^{24}$ or $-O-N=CR^{25}R^{26}$, wherein $R^{13}$ and $R^{15}$ are halogen or trifluoromethyl, $R^{14}$, $R^{16}$, $R^{17}$, $R^{18}$ and $R^{19}$ are hydrogen or halogen, each of $R^{20}$ and $R^{21}$, independently of the other, is hydrogen, $C_1-C_8$alkoxy, $C_1-C_8$alkyl, phenyl or benzyl, or $R^{20}$ and $R^{21}$ together with the nitrogen atom carrying them form a 5- or 6-membered saturated nitrogen heterocycle that may be interrupted by an oxygen or a sulfur atom, $R^{22}$ is $C_1-C_4$alkyl, $C_3-C_4$alkenyl, $C_3-C_4$alkynyl or $C_2-C_4$-alkoxyalkyl, $R^{23}$ is hydrogen or the equivalent of an alkali metal, alkaline earth metal, copper or iron ion; a quaternary $C_1-C_4$alkylammonium or $C_1-C_4$hydroxyalkylammonium radical; a $C_1-C_9$alkyl radical which is unsubstituted or mono- or poly-substituted by amino, halogen, hydroxy, cyano, nitro, phenyl, $C_1-C_4$alkoxy, polyethoxy having from 2 to 6 ethylene oxide units, $-COOR^{27}$, $-COSR^{28}$, $-CONH_2$, $-CON(C_1-C_4alkoxy)-C_1-C_4alkyl$, $-CO-N-di-C_1-C_4alkyl$, $CONH-C_1-C_4alkyl$, $-N(C_1-C_4alkoxy)-C_1-C_4alkyl$ or by di-$C_1-C_4$alkylamino; a $C_3-C_9$alkenyl radical which is unsubstituted or substituted by halogen or by $C_1-C_4$alkoxy; a $C_3-C_9$alkynyl radical which is unsubstituted or substituted by halogen or by $C_1-C_4$alkoxy; $C_3-C_9$cycloalkyl; or phenyl which is unsubstituted or substituted by cyano, $C_1-C_4$-alkyl, $C_1-C_4$alkoxy, acetyl, $-COOR^{29}$, $COSR^{30}$, $-CONH_2$, $-CON(C_1-C_4alkoxy)-C_1-C_4alkyl$, $-CO-N-di-C_1-C_4alkyl$ or by $-CONH-C_1-C_4alkyl$, each of $R^{25}$ and $R^{26}$, independently of the other, is $C_1-C_4$alkyl, or $R^{25}$ and $R^{26}$ together form a 3- to 6-membered alkylene chain, and each of $R^{27}$, $R^{28}$, $R^{29}$ and $R^{30}$, independently of the others, is hydrogen, $C_1-C_6$alkyl, $C_1-C_6$haloalkyl, $C_2-C_6$alkoxyalkyl, $C_3-C_6$alkenyl, $C_3-C_6$haloalkyl, $C_3-C_6$alkynyl or $C_3-C_6$-haloalkynyl. The substituents $R^{15}$ and $R^{16}$ are preferably halogen.

Preferred herbicidal aryloxyphenoxypropionic acid derivatives of formula IV are those where Q is a radical wherein $R^{15}$ and $R^{16}$ are halogen and $R^{17}$, $R^{18}$, $R^{19}$ and T are as defined above for formula IV.

The following herbicidal aryloxphenoxypropionic acid derivatives especially fall within the scope of formula IV: 2-[4-(3,5-dichloropyridin-2-yloxy)-phenoxy]-propionic acid propargyl ester, 2-[4-(3,5-dichloropyridin-2-yloxy)-phenoxy]-thiopropionic acid propargyl ester, 2-[4-(5-chloro-3-fluoropyridin-2-yloxy)-phenoxy]-propionic acid propargyl ester, 2-[4-(5-chloro-3-fluoropyridin-2-yloxy)phenoxy]-propionic acid methyl ester, 2-[4-(5-chloro-3-fluoropyridin-2-yloxy)-phenoxy]-propionic acid butyl ester, 2-[4-(5-trifluoromethylpyridin-2-yloxy)-phenoxy]-propionic acid butyl ester, 2-[4-(5-trifluoromethylpyridin-2-yloxy)-phenoxy]-propionic acid methyl ester, 2-[4-(6-chloroquinoxalin-2-yloxy)-phenoxy]-propionic acid ethyl ester and 2-[4-(6- chlorobenzoxazolin-2-yloxy)-phenoxy]-propionic acid ethyl ester.

Contingent upon the asymmetric substitution at the α-carbon atom of the propionic acid, the aryloxyphenoxypropionic acid derivatives of formula IV may occur in two different stereoisomeric forms. The invention relates to the use of compounds of formula I as antidotes to both the racemates of compounds of formula IV and the optical isomers of compounds of formula IV. Optical isomers of compounds of formula IV are described inter alia in U.S. Pat. No. 4,505,743 which relates to D(+) isomers of formula IV. The compounds of formula I can also be used espeically advantageously in the case of the R-isomers of formula IV which are known from EP-A-0 248 968. Attention is especially drawn in this connection to 2R-2-[4-(5-chloro-3-fluoropyrid-2-yloxy)-phenoxy]-propionic acid propargyl ester.

The N-benzoyl-N-phenylalanines whose harmful effect on cultivated plants is antagonised by the compounds of formula I have the formula V

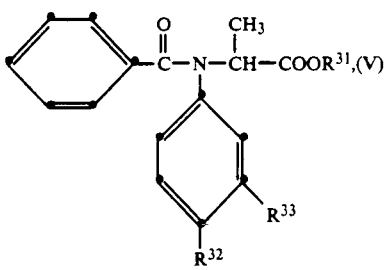

wherein $R^{31}$ is hydrogen or $C_1$–$C_4$alkyl and each of $R^{32}$ and $R^{33}$, independently of the other, is fluorine or chlorine.

Individual compounds of formula V that are to be mentioned are: N-benzoyl-N-(3,4-dichlorophenyl)alanine ethyl ester and N-benzoyl-N-(3-chloro-4-fluorophenyl)alanine methyl ester.

The compounds of formula V are known per se (R. Wegler; Chemie der Pflanzenschutz- und Schädlingsbekämpfungsmittel, vol. 5, Springer Verlag, Berlin 1977, pp. 194–195). The antidotes of formula I can be used successfully both in the case of the racemic compounds of formula V and in the case of their enantiomers.

The antidotes of formula I are most especially suitable for protecting cultivated plants from the harmful effects of herbicides of formulae II, III, IV and V.

The present invention also relates to a method of protecting cultivated plants from the harmful effect of herbicides, which comprises treating the cultivated plant or the locus thereof or seeds or cuttings of the cultivated plant with an antagonistically effective amount of a compound of formula I before, during or after application of the herbicide.

Agrochemical compositions that contain in a common formulation together with the antidote of formula I a herbicide, especially a sulfonylurea herbicide, an N-benzoyl-N-phenylalanine herbicide, a chloroacetanilide herbicide or an aryloxyphenoxypropionic acid herbicide, are suitable for use as selective herbicides in crops of useful plants. The herbicidal compositions of the invention preferably contain, in addition to an antidote of formula I, a sulfonylurea of formula II, a chloroacetanilide of formula III, an aryloxyphenoxypropionic acid derivative of formula IV or an N-benzoyl-N-phenylalanine of formula V as herbicides. Preferred partners in the mixture are the antidotes of formula I. given prominence hereinabove and the herbicides of the formulae II, III, IV and V given prominence for use hereinabove.

Unless used for dressing seeds, the amount of safener applied varies between about 0.01 and about 100 parts by weight per part by weight of herbicide, and is preferably in the range from 0.1 to about 10 parts by weight of compound of formula I per part by weight of herbicide. In practice, the most suitable ratio for achieving the optimum effect in the particular cultivated plant is determined from case to case, i.e. depending on the type of herbicide employed.

The invention relates also to compositions that contain a compound of formula I' together with one or more adjuvants, carriers or adjuvants/carriers.

The invention relates also to a method of selectively controlling weeds in crops of cultivated plants, which comprises treating the crops of cultivated plants, parts of the cultivated plants or the cultivation areas of the cultivated plants with a herbicide and a compound of formula I or with a composition containing that combination. The present invention relates also to the compositions containing the combination of herbicide and antidote.

The weeds to be controlled may be either monocotyledonous or dicotyledonous weeds.

Weeds that should be mentioned especially are weeds of the genera Echinochloa, Rottboellia, Digitaria and Setaria.

Various methods and techniques are suitable for employing the compounds of formula I or compositions containing them for the protection of cultivated plants from the harmful effects of agrochemicals. Examples of these methods and techniques are:

i) Seed dressing a) dressing the seed with an active ingredient formulated as a wettable powder, by shaking in a vessel until uniform distribution over the surface of the seed is achieved (dry dressing). In this procedure, about 0.1 to 2.0 g of active ingredient of formula I (0.4 g to 8.0 g of wettable powder in the case of a 25% strength formulation) are used per 1 kg of seed.

b) dressing the seed with an emulsifiable concentrate of the active ingredient or with an aqueous solution of a wettable powder formulation of the active ingredient of formula I by method a) (wet dressing).

c) dressing by immersing the seed in a liquor containing from 10 to 1000 ppm of an active ingredient of formula I for from 1 to 72 hours and, if desired, subsequently drying the seed (immersion dressing, seed soaking).

Dressing the seed or treating the sprouted seedlings are, of course, the preferred methods of application since the treatment with the active ingredient is directed entirely towards the target crop. As a rule, from 0.01 g to 6.0 g, preferably from 0.1 g to 2.0 g, of active ingredient are used per 1 kg of seed, and, depending on the method employed, which also allows other active ingredients or micronutrients to be added, it is possible to exceed or use less than the concentration limits indicated (repeat dressing).

ii) Application from a tank mixture

A liquid formulation of a mixture of safener and herbicide (ratio of the one to the other between 100:1 and 1:100, preferably 10:1 to 1:10) is used, the application rate of herbicide and safener being in each case from 0.001 to 10 kg per hectare. A tank mixture of this type is preferably applied before or after sowing and, when applied before sowing, is worked 5 to 10 cm deep into the as yet unsown soil.

iii) Application to the seed furrow

The safener is introduced in the form of an emulsifiable concentrate, wettable powder or granulate into the open, sown seed furrow and then, after the seed furrow has been covered in the normal manner, the herbicide is applied according to the pre-emergence method.

iv) Controlled release of active ingredient

A solution of the active ingredient is adsorbed onto mineral granulate carriers or polymerised granules (urea/formaldehyde) and is allowed to dry. If desired, it is possible to apply a coating (coated granulate) which allows the active ingredient to be released in metered amounts over a specific period of time.

The compounds of formula I are used in unmodified form or, preferably, together with the adjuvants conventionally employed in the art of formulation, and are therefore formulated e.g. into emulsifiable concentrates, directly sprayable or dilutable solutions, dilute emulsions, wettable powders, soluble powders, dusts, granulates, and also encapsulations. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the active ingredient of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the active ingredient of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical, alkyl also including the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are especially polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenolpolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are especially quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, inter alia, in the following publications: "1986 International McCutcheon's Emulsifiers & Detergents", Glen Rock, N.J. U.S.A., 1986, H. Stache, "Tensid-Taschenbuch", 2nd edition, C. Hanser Verlag, Munich, Vienna 1981, M. and J. Ash, "Encyclopedia of Surfactants" Vol. I–III, Chemical Publishing Co., New York, 1980–1981.

The possible formulations disclosed above can be used not only for antidotes of formula I but generally also for active ingredient mixtures of antidotes of formula I and herbicides, especially herbicides of the formulae II, III, IV and V.

The agrochemical preparations usually contain 0.1 to 95%, preferably 0.1 to 80%, of an active ingredient of formula I or of a mixture of antidote and herbicide, 1 to 99.9% of a solid or liquid adjuvant, and 0 to 25%, preferably 0.1 to 25%, of a surfactant.

Preferred formulations are composed especially of the following constituents (throughout, percentages are by weight):

| Emulsifiable concentrates: | |
|---|---|
| active ingredient mixture: | 1 to 20%, preferably 5 to 10% |
| surfactant: | 5 to 30%, preferably 10 to 20% |
| liquid carrier: | 50 to 94%, preferably 70 to 85% |
| Dusts: | |
| active ingredient mixture: | 0.1 to 10%, preferably 0.1 to 1% |
| solid carrier: | 99.9 to 90%, preferably 99.9 to 99% |
| Suspension concentrates: | |
| active ingredient mixture: | 5 to 75%, preferably 10 to 50% |
| water: | 94 to 25%, preferably 88 to 30% |
| surfactant: | 1 to 40%, preferably 2 to 30% |
| Wettable powders: | |
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |
| Granulates: | |
| active ingredient mixture: | 0.5 to 30%, preferably 3 to 15% |
| solid carrier: | 99.5 to 70%, preferably 97 to 85% |

Whereas commercial preparations will preferably be formulated as concentrates, the end user will normally employ dilute formulations. The formulations may be diluted to a concentration of as little as 0.001% active ingredient. The rates of application are normally from 0.01 to 10 kg a.i./ha, preferably from 0.25 to 5 kg a.i./ha.

The compositions may also contain further ingredients, such as stabilisers, antifoams, preservatives, viscosity regulators, binders, tackifiers and also fertilisers or other active ingredients for obtaining special effects.

The novel compounds of formula I'

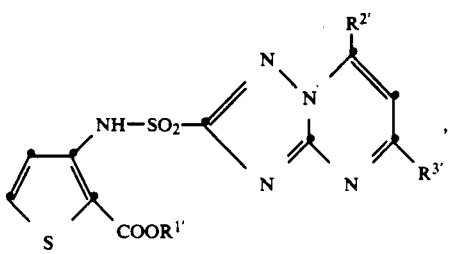

which can be used according to the invention and wherein $R^{1'}$ is $C_1$–$C_6$-alkyl or $C_3$–$C_6$cycloalkyl, and each of $R^{2'}$ and $R^{3'}$, independently of the other, is hydrogen, $C_1$–$C_3$alkyl, trifluoromethyl or cyclopropyl, with the proviso that at least one of the symbols $R^{2'}$ and $R^{3'}$ is cyclopropyl, can be prepared by reacting a compound of formula VI

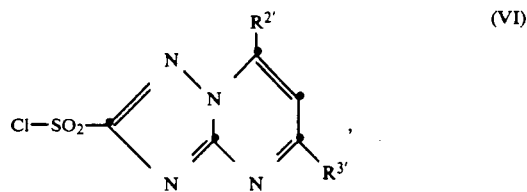

wherein each of $R^{2'}$ and $R^{3'}$, independently of the other, is hydrogen, $C_1$–$C_3$alkyl, trifluoromethyl or cyclopropyl, with the proviso that at least one of the symbols $R^{2'}$ and $R^{3'}$ is cyclopropyl, with a compound of formula VII

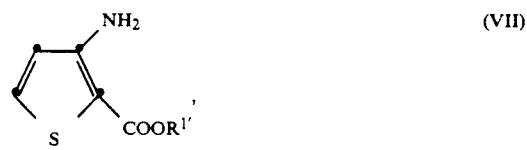

wherein $R^{1'}$ is $C_1$–$C_6$alkyl or $C_3$–$C_6$cycloalkyl.

The reaction is advantageously carried out within a temperature range of from 5° C. to 25° C. and in the presence of a base, such as, for example, pyridine or a tertiary amine, such as 4-dimethylaminopyridine, N-methylmorpholine or triethylamine. The reaction is preferably carried out in a solvent that is inert towards the reaction, such as, for example, pyridine, dichloromethane or acetonitrile. Advantageously, the reactants of formulae VI and VII are employed in an equimolar ratio to each other or a slight excess of the compound of formula VI is used.

The intermediates of formulae VII are known or can be prepared analogously to known compounds.

The intermediates of formula VI can be obtained by treating a compound of formula VIII

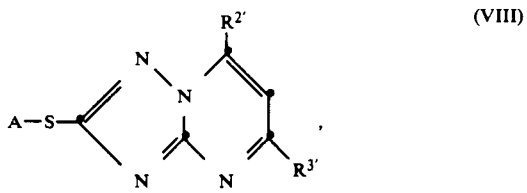

wherein each of $R^{2'}$ and $R^{3'}$, independently of the other, is hydrogen, $C_1$–$C_3$alkyl, trifluoromethyl or cyclopropyl, with the proviso that at least one of the symbols $R^{2'}$ and $R^{3'}$ is cyclopropyl, and A is hydrogen or benzyl, with chlorine in an aqueous acidic medium. The acid used is an organic acid, especially acetic acid, or preferably an inorganic acid, especially hydrochloric acid. The treatment with chlorine is carried out advantageously at temperatures in the range of from −25° C. to 20° C., preferably at from −15° C. to 0° C. The treatment with chlorine is preferably carried out with the addition of dichloromethane to the medium.

The intermediates of formula VIII can be prepared by reacting a compound of formula IX

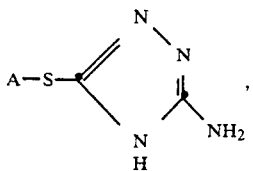

(IX)

wherein A is hydrogen or benzyl, with a compound of formula X $$R_b—CO—CH_2—R_a \qquad (X),$$

wherein i) $R_a$ is a group $—CO—R_c$ and one of the symbols $R_b$ and $R_c$ is $R^{2'}$ and the other is $R^{3'}$, or ii) $R_a$ is a group $—CH(OR_d)_2$ and $R_b$ is $R^{2'}$ or $R^{3'}$ and $R_d$ is methyl or ethyl.

The intermediates of formulae IX and X are known or can be prepared analogously to known methods. The compound of formula IX wherein A is benzyl can be prepared, for example, in a manner known per se by reacting a compound of formula IX wherein A is hydrogen with benzyl chloride.

The reaction of a compound of formula IX with a compound of formula X is advantageously carried out by first dissolving a compound of formula IX in a small amount of glacial acetic acid while heating and, following the addition of the compound of formula X, heating the reaction mixture at reflux temperature.

The intermediates of formula VI and VIII which have been developed for the preparation of compounds of formula I' are novel and the present invention relates to them also.

The compounds of formula I that do not fall within the scope of formula I' can be prepared analogously to the methods indicated for compounds of formula I'.

The following Examples serve to illustrate the invention without implying any limitation thereof.

EXAMPLE P1

Preparation of N-(5-methyl-7-cyclopropyl-1,2,4-triazolo[1,5-a]pyrimidin-2-ylsulfonyl)-3-aminothiophene-2-carboxylic acid methyl ester a) 5-methyl-7-cyclopropyl-1,2,4-triazolo[1,5-a]pyrimidin-2-yl sulfochloride 35 g of 2-benzylthio-5-methyl-7-cyclopropyl-1,2,4-triazolo[1,5-a]pyrimidine in 200 ml of dichloromethane are stirred with 300 ml of water and 20 ml of concentrated hydrochloric acid. 33.5 g of chlorine gas are introduced into the mixture at from 0° C. to −3° C. After about 30 minutes, the introduction of gas is complete and the reaction mixture is then stirred for about 20 minutes without cooling. After diluting with water, the organic phase is separated, dried over sodium sulfate and concentrated by evaporation in vacuo. The resulting oil is washed with several portions of petroleum ether. Drying yields 5-methyl-7-cyclopropyl-1,2,4-triazolo[1,5-a]pyrimidin-2-yl sulfochloride in the form of a crude product that is suitable for the further reactions. Yield: 28 g of dark oil.

b) N-(5-methyl-7-cyclopropyl-1,2,4-triazolo[1,5-a]pyrimidin-2-ylsulfonyl)-3-aminothiophene-2-carboxylic acid methyl ester 14 g of N-5-methyl-7-cyclopropyl-1,2,4-triazolo[1,5-a]pyrimidin-2-yl sulfochloride (crude product from part a)) in 15 ml of pyridine are stirred with 7.9 g of 3-aminothiophene-2-carboxylic acid methyl ester. After dissolving with a slightly exothermic reaction, the reaction mixture becomes dark in colour. After leaving to stand for a prolonged period, a slight precipitate forms. The reaction mixture is then diluted with about 100 ml of ethyl acetate/hexane 1:1 and 300 ml of water and rendered strongly alkaline with soda. The aqueous phase is separated and acidified with hydrochloric acid. The resulting precipitate is collected and dried (19 g). The product is recrystallised from acetone/hexane to yield 14.8 g of N-(5-methyl-7-cyclopropyl-1,2,4-triazolo[1,5-a]pyrimidin-2-ylsulfonyl)-3-aminothiophene-2-carboxylic acid methyl ester. M.p. 185°–187° C. (decoposition).

EXAMPLE P2

Preparation of N-(5-cyclopropyl-7-methyl-1,2,4-triazolo[1,5-a]pyrimidin-2-ylsulfonyl)-3-aminothiophene-2-carboxylic acid methyl ester a) 5-cyclopropyl-7-methyl-1,2,4-triazolo[1,5-a]pyrimidin-2-yl sulfochloride 14 g of 2-benzylthio-5-cyclopropyl-7-methyl-1,2,4-triazolo[1,5-a]pyrimidine in 200 ml of dichloromethane and 200 ml of water are mixed with 10 ml of concentrated hydrochloric acid and stirred vigorously. 13.5 g of chlorine gas are introduced at from 0° C. to −3° C. over a period of about 20 minutes. After subsequently stirring for about half an hour without cooling, the organic phase is separated, washed with water and dried over sodium sulfate. Concentration by evaporation in vacuo yields a dark oil which is stirred several times with petroleum ether. The petroleum ether is decanted off and the resulting viscous residue is dried to yield 11.5 g of 5-cyclopropyl-7-methyl-1,2,4-triazolo[1,5-a]pyrimidin-2-yl sulfochloride in the form of a dark oil (crude product) that is suitable for the further reactions. The proton resonance spectrum confirms the constitution of the compound obtained.

b) N-(5-cyclopropyl-7-methyl-1,2,4-triazolo[1,5-a]pyrimidin-2-ylsulfonyl)-3-aminothiophene-2-carboxylic acid methyl ester 5.7 g of 5-cyclopropyl-7-methyl-1,2,4-triazolo[1,5-a]pyrimidin-2-yl sulfochloride (crude product from part a)) are stirred in 15 ml of pyridine with 3.5 g of 3-aminothiophene-2-carboxylic acid methyl ester. The further treatment of the reaction mixture is carried out as described in Example 1 (part b). 4.8 g of N-(5-cyclopropyl-7-methyl-1,2,4-triazolo[1,5-a]pyrimidin-2-ylsulfonyl)-3-aminothiophene-2-carboxylic acid methyl ester are obtained. M.p. 133°–134.5° C.

EXAMPLE P3

Preparation of 2-benzylthio-5-methyl-7-cyclopropyl-1,2,4-triazolo[1,5-a]pyrimidine (compound A) and 2-benzylthio-5-cyclopropyl-7-methyl-1,2,4-traizolo[1,5-a]pyrimidine (compound B)

41.5 g of 3-amino-5-benzylthio-1,2,4-triazole are dissolved in a small amount of hot glacial acetic acid and heated under reflux together with 30 g of 1-cyclopropyl-1,3-butanedione. After about 1 hour, the reaction solution is concentrated in vacuo and water is added to the residue. The resulting dark resin is extracted with ethyl acetate and the ethyl acetate phase is dried over sodium sulfate and concentrated by evaporation. The residue is purified over a column of silica gel (eluant :ethyl acetate/hexane 1:1). Title compounds A and B are obtained: 1st Fraction 20 g m.p. 101°-103° C. (compound B) 2nd Fraction 39 g m.p. 84°-86° C. (compound A).

The following compounds of formula I (end products, Table 1), together with compounds of the preceding Examples, and also those of formulae VI (intermediates, Table 2) and VIII (intermediates, Table 3) are prepared analogously to the procedures described:

TABLE 1

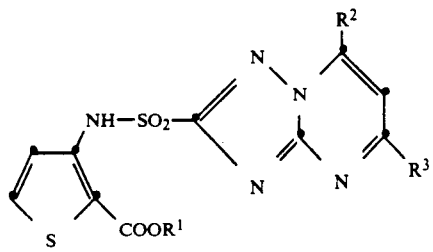

| comp. no. | $R^1$ | $R^2$ | $R^3$ | phys. data/m.p. |
|---|---|---|---|---|
| 1.01 | $CH_3$ | cyclopropyl | $CH_3$ | 185-187° C. |
| 1.02 | $CH_3$ | $CH_3$ | cyclopropyl | 133-134° C. |
| 1.03 | $CH_3$ | H | $CH_3$ | 213-214° C. |
| 1.04 | $CH_3$ | $CH_3$ | $CH_3$ | 164-165° C. |
| 1.05 | $C_2H_5$ | $CH_3$ | $CH_3$ | 181-183° C. |
| 1.06 | $C_6H_{13}$ | $CH_3$ | $CH_3$ | |
| 1.07 | $C_4H_9$ | $CH_3$ | $CH_3$ | |
| 1.08 | $C_2H_5$ | cyclopropyl | $CH_3$ | |
| 1.09 | $C_2H_5$ | $CH_3$ | cyclopropyl | |
| 1.10 | $C_2H_5$ | H | cyclopropyl | |
| 1.11 | $C_2H_5$ | cyclopropyl | H | |
| 1.12 | $CH_3$ | H | cyclopropyl | |
| 1.13 | $CH_3$ | cyclopropyl | H | |
| 1.14 | $CH_3$ | $CH_3$ | H | |
| 1.15 | $C_3H_7(i)$ | $CH_3$ | $CH_3$ | 164-167° C. |
| 1.16 | $C_2H_5$ | H | $CH_3$ | |
| 1.17 | $CH_3$ | $CH_3$ | H | 158-160° C. |
| 1.18 | $C_2H_5$ | H | $CH_3$ | 137-139.5° C. |
| 1.19 | $CH_3$ | cyclopropyl | cyclopropyl | 184-186° C. |
| 1.20 | $CH_3$ | $CF_3$ | cyclopropyl | |

TABLE 2

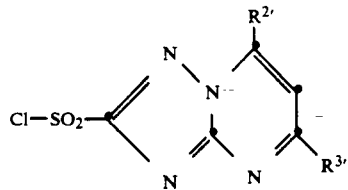

| comp. no. | $R^{2'}$ | $R^{3'}$ | physical data |
|---|---|---|---|
| 2.01 | H | cyclopropyl | |
| 2.02 | cyclopropyl | H | |
| 2.03 | $CH_3$ | cyclopropyl | oil |
| 2.04 | cyclopropyl | $CH_3$ | oil |
| 2.05 | cyclopropyl | cyclopropyl | 127.5-130° C. |
| 2.06 | $CF_3$ | cyclopropyl | 78-81° C. |

TABLE 3

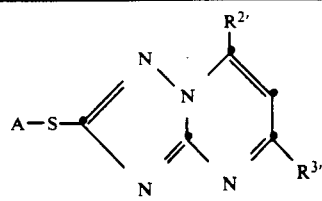

| comp. no. | A | $R^{2'}$ | $R^{3'}$ | phys. data/m.p. |
|---|---|---|---|---|
| 3.01 | H | H | cyclopropyl | |
| 3.02 | H | cyclopropyl | H | |
| 3.03 | benzyl | cyclopropyl | H | 82-86° C. |
| 3.04 | benzyl | cyclopropyl | $CH_3$ | 84-86° C. |
| 3.05 | benzyl | $CH_3$ | cyclopropyl | 101-103° C. |
| 3.06 | benzyl | H | cyclopropyl | 112-114° C. |
| 3.07 | benzyl | $CF_3$ | cyclopropyl | 123-124° C. |
| 3.08 | benzyl | cyclopropyl | cyclopropyl | 96-98° C. |

BIOLOGICAL EXAMPLES

B1. Safening action in paddy rice

In order to test the safening action, rice seeds (variety YAMABIKO, NIHONBARE) are sown in seed trays filled with garden soil that has been watered in the normal manner. At the 2-leaf stage, the plants are transplanted into containers of extremely swampy soil. The water level is raised as growth increases. The plants are cultivated in a greenhouse under suitable conditions of temperature and light. The plants are watered and fertilised as required.

The safener is added to the swampy soil 7 days before transplantation and the herbicide is applied by being poured into the water 3 days after transplantation.

In order to determine the safening action (protective action) the general damage to the plants is assessed 10 days after applying the herbicide (phytotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

The results for the herbicide of formula II

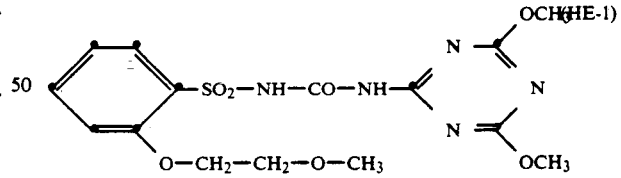

N-[2-(2-methoxyethoxy)-phenylsulfonyl]-N'-4,6-dimethoxy-1,3,5-triazin-2-ylurea (known from EP-A-0 044 807 and EP-A-0 224 441) (herbicide HE-1) and the safener of formula I N-(5,7-dimethyl-1,2,4-triazolo[1,5-a]pyrimidin-2-ylsulfonyl)-3-aminothiophene-2-carboxylic acid methyl ester (safener S-1) are set forth in Table 4:

TABLE 4

| application rates | protective action in % |
|---|---|
| 100 ppm S-1; 260 g/ha HE-1 | rice of the variety |
| | "YAMABIKO"  "NIHONBARE" |
| | 20  30 |

B2. Safening action in paddy rice (tank mixture)

In order to test the safening action, rice seeds (variety S-201) are raised in swampy soil in pots of 9×9 cm (diameter×height). The plants are cultivated in a greenhouse under suitable conditions of temperature and light. The plants are watered and fertilised as required.

Safener and herbicide are applied together in the form of a tank mixture, at an application rate corresponding to 550 liters of water per hectare, directly after sowing (PRE) or 3 days after sowing (3 DAS).

In order to determine the safening action (protective action) the general damage to the plants is assessed 24 days after application of the active ingredient mixture (phytotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

The active ingredients used are the substances employed in Example B1 (herbicide HE-1 and safener S-1). The results are shown in Table 5.

TABLE 5

| time of application | PRE | | 3 DAS | |
|---|---|---|---|---|
| HE-1 application rate [g/ha] | 30 | | 30 | |
| S-1 application rate [g/ha] | 120 | 60 | 120 | 60 |
| protective action in % | | | | |
| in rice of the variety "S-201" | 40 | 45 | 60 | 60 |

B3. Safening action in cereals (tank mixture)

In order to test the safening action, wheat seeds (variety BESSO) and barley (variety CORNEL) are raised in soil in pots of 11 cm diameter. The plants are cultivated in a greenhouse under suitable conditions of temperature and light. The plants are watered and fertilised as required.

Safener and herbicide are applied together post-emergence in the form of a tank mixture, at an application rate corresponding to 550 liters of water per hectare.

In order to determine the safening action (protective action) the general damage to the plants is assessed 18 days after application of the active ingredient mixture (phytotoxicity 0%: no damage, condition as that of untreated controls; phytotoxicity 100%: maximum damage). The protective action, expressed in %, is found from the difference between the phytotoxicity caused by application of the herbicide alone and the phytotocicity occurring when herbicide and safener are applied.

The results for the following herbicides of formula IV

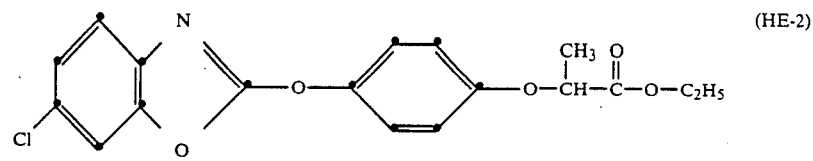

2-[4-(6-chlorobenzoxazol-2-yloxy)phenoxy]propionic acid ethyl ester (The Pesticide Manual; 8th edition, British Crop Protection Council, Thornton Heath, 1987, comp. no. 6160).

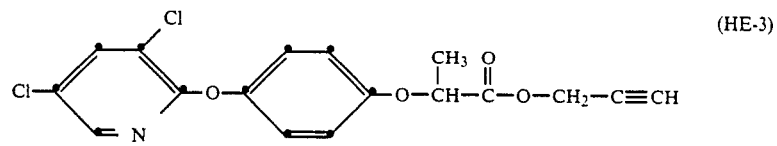

2-[4-(3,5-dichloropyridin-2-yloxy)phenoxy]-propionic acid propargyl ester (known from EP-A-0 003 114) and

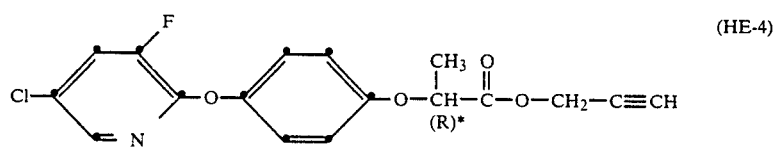

2R-2-[4-(5-chloro-3-fluoropyridin-2-yloxy)phenoxy]-propionic acid propargyl ester (known from EP-A-0 248 968) and the safener S-1 from Example 1 are set forth in Table 6:

TABLE 6

| herbicide | HE-2 | | HE-3 | | HE-4 | |
|---|---|---|---|---|---|---|
| application rate [g/ha] | 1000 | | 1000 | | 120 | |
| safener S-1 application rate [g/ha] | 2000 | 500 | 2000 | 500 | 2000 | 500 |
| protective action in % in | | | | | | |
| wheat of the variety "BESSO" | 50 | 55 | 73 | 48 | 60 | 35 |
| barley of the variety "CORNEL" | 60 | 70 | 33 | 28 | — | — |

B4. Safening action in rice (tank mixture)

In order to test the safening action, rice seeds (variety NEWBONNET) are raised in soil in pots of 11 cm diameter. The plants are cultivated in a greenhouse under suitable conditions of temperature and light. The plants are watered and fertilised as required. The weed Echinochloa is raised by the same method.

Safener and herbicide are applied together post-emergence in the form of a tank mixture, at an application rate corresponding to 550 liters of water per hectare, the test plants being used at various stages of growth.

In order to determine the safening action (protective action) the general damage to the plants is assessed 23 days after application of the active ingredient mixture (phytotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

The results for the herbicide HE-4 (according to Example B3) and the safener S-1 (according to Example B1) are set forth in Table 7:

TABLE 7

| time of application | 1- to 2-leaf stage | | | 2- to 3-leaf stage | | | 4-leaf stage | | |
|---|---|---|---|---|---|---|---|---|---|
| herbicide HE-4 application rate [g/ha] | 60 | | | 60 | | | 60 | | |
| safener S-1 application rate [g/ha] | 480 | 120 | 30 | 480 | 120 | 30 | 480 | 120 | 30 |
| protective action in % | | | | | | | | | |
| in rice of the variety "NEWBONNET" | 60 | 35 | 40 | 60 | 60 | 50 | 80 | 45 | 40 |
| Echinochloa crus galli | 2 | 0 | 0 | 2 | 0 | 0 | 5 | 1 | 0 |

B5. Safening action in rice (tank mixture)

In order to test the safening action, rice seeds (varieties NEWBONNET, BALILLA, JUNG-WEON, PB 56, IR54, YAMABIKO, STARBONNET) are raised in soil in pots of 11 cm diameter. The plants are cultivated in a greenhouse under suitable conditions of temperature and light. The plants are watered and fertilised as required. The weeds Echinochloa, Rottboellia and Digitaria are raised by the same method.

Safener and herbicide are applied together post-emergence in the form of a tank mixture, at an application rate corresponding to 550 liters of water per hectare.

In order to determine the safening action (protective action) the general damage to the plants is assessed 23 days after application of the active ingredient mixture (phytotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

The results indicated in Table 8 are obtained for the herbicide/safener combination (according to Example B4):

TABLE 8

| herbicide HE-4 application rate [g/ha] | 60 | | |
|---|---|---|---|
| safener S-1 application rate [g/ha] | 480 | 120 | 30 |
| protective action in % | | | |
| rice of the varieties | | | |
| "NEWBONNET" | 50 | 40 | 35 |
| "BALILLA" | 90 | 65 | 50 |
| "JUNG-WEON" | 55 | 60 | 60 |
| "PB 56" | 60 | 50 | 45 |

TABLE 8-continued

| herbicide HE-4 application rate [g/ha] | 60 | | |
|---|---|---|---|
| safener S-1 application rate [g/ha] | 480 | 120 | 30 |
| "IR 54" | 45 | 40 | 35 |
| "YAMABIKO" | 60 | 20 | 25 |
| "STARBONNET" | 60 | 45 | 35 |
| Echinochloa c.g. | 0 | 0 | 0 |
| Rottboellia exaltata | 0 | 0 | 0 |
| Digitaria sang. | 8 | 8 | 3 |

B6. Safening action in rice (tank mixture)

In order to test the safening action, rice seeds (variety S-201) are raised in soil in pots of 12 cm diameter. The plants are cultivated in a greenhouse under suitable conditions of temperature and light. The plants are watered and fertilised as required. The weed Setaria italica is raised by the same method.

Safener and herbicide are applied together post-emergence in the form of a tank mixture, at an application rate corresponding to 550 liters of water per hectare, the tank mixture being used to treat rice in the 1- to 2-leaf stage and Setaria in the 3-leaf stage.

In order to determine the safening action (protective action) the general damage to the plants is assessed 10 days after application of the active ingredient mixture (phytotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

In addition to the herbicides HE-2 and HE-4 (according to Example B3), the following herbicides are used as herbicides of formula IV in combination with the safener S-1 known from Example 1

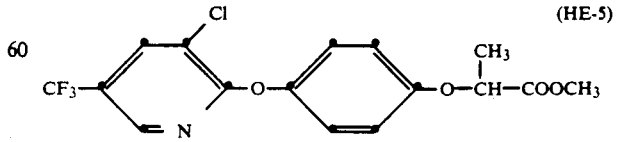
(HE-5)

2-[4-(3-chloro-5-trifluoromethylpyridin-2-yloxy)-phenoxy]-propionic acid methyl ester (The Pesticide Manual, 8th edition; The British Crop Protection Council, Thornton Heath, 1987, comp. no. 7010) and

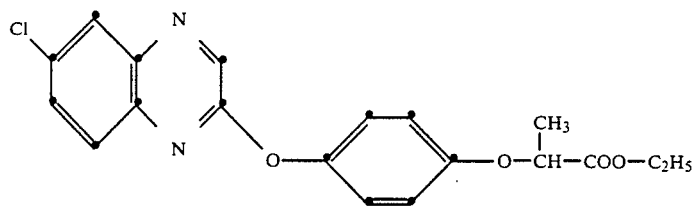
(HE-6)

2-[4-(6-chloroquinoxalin-2-yloxy)phenoxy]-propionic acid ethyl ester (The Pesticide Manual, 8th edition; The British Crop Protection Council, Thornton Heath, 1987, comp. no. 10 565); and the following herbicide as herbicide of formula III in combination with the safener S-1 known from Example 1

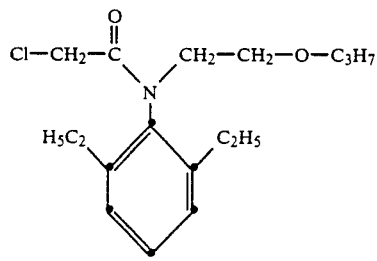
(HE-7)

2-chloro-2',6'-diethyl-N-(2-propoxyethyl)-acetanilide (The Pesticide Manual, 8th edition; The British Crop Protection Council, Thornton Heath, 1987, comp. no. 9970).

The results are set forth in Table 9.

TABLE 9

| herbicide | HE-2 | HE-4 | HE-5 | HE-6 | HE-7 |
|---|---|---|---|---|---|
| application rate [g/ha] | 128 | 64 | 128 | 64 | 512 |
| safener S-1 |  |  |  |  |  |
| application rate [g/ha] | 100 | 100 | 100 | 100 | 100 |
| protective action in % |  |  |  |  |  |
| in rice of the variety "S-201" | 35 | 20 | 25 | 90 | 35 |
| Setaria italica | 0 | 7 | 1 | 2 | 0 |

B7. Safening action in paddy rice (tank mixture)

In order to test the safening action, rice seeds (variety NEWBONNET) are raised in swampy soil in pots of 9×9 cm (diameter×height). The plants are cultivated in a greenhouse under suitable conditions of temperature and light. The plants are watered and fertilised as required.

Safener and herbicide are applied together post-emergence in the form of a tank mixture, at an application rate corresponding to 550 liters of water per hectare, the rice plants being treated in the 1- to 2-leaf stage.

In order to determine the safening action (protective action) the general damage to the plants is assessed 21 days after application of the active ingredient mixture (phyotoxicity 0%: no damage, condition as that of untreated controls; phytotoxicity 100%: maximum damage). The protective action, expressed in %, is found from the difference between the phytotoixcity caused by application of the herbicide alone and the phytotoxicity occurring when herbicide and safener are applied.

As active ingredients there are used the herbicide HE-4 employed in Example B3 and the following safeners of formula I:

N-(5-methyl-1,2,4-triazolo[1,5-a]pyrimidin-2-ylsulfonyl)-3-aminothiophene-2-carboxylic acid methyl ester (S-2), N-(5-methyl-7-cyclopropyl-1,2,4-triazolo[1,5-a]pyrimidin-2-ylsulfonyl)-3-aminothiophene-2-carboxylic acid methyl ester (S-3), N-(5-cyclopropyl-7-methyl-1,2,4-triazolo[1,5a]pyrimidin-2-ylsulfonyl)-3-aminothiophene-2-carboxylic acid methyl ester (S-4) and the safener S-1 used in Example B1. The results are shown in Table 10.

TABLE 10

| HE-4 appl. rate [g/ha] | 120 | | | | 60 | | | |
|---|---|---|---|---|---|---|---|---|
| S-2 appl. rate [g/ha] | 480 | 240 | 120 | | 480 | 240 | 120 | |
| protective action in %: | 37 | 25 | 25 | | 25 | 25 | 37 | |
| S-3 or S-4 or S-1 | | | | | | | | |
| application rate [g/ha] | 400 | 100 | 25 | 6 | 400 | 100 | 25 | 6 |
| S-3, protec. action in %: | 50 | 37 | 12 | 12 | 50 | 50 | 25 | 12 |
| S-4, protec. action in %: | 33 | 12 | 12 | 0 | 60 | 55 | 30 | 25 |
| S-1, protec. action in %: | 60 | 40 | 40 | 20 | 60 | 60 | 45 | 30 |

B8. Safening action in paddy rice (tank mixture)

In order to test the safening action, rice seeds (variety S-201) are raised in swampy soil in pots of 9×9 cm (diameter×height). The plants are cultivated in a greenhouse under suitable conditions of temperature and light. The plants are watered and fertilised as required.

Safener and herbicide are applied together pre-emergence in the form of a tank mixture, at an application rate corresponding to 550 liters of water per hectare.

In order to determine the safening action (protective action) the general damage to the plants is assessed 21 days after application of the active ingredient mixture (phyotoxicity 0%: no damage, condition as that of untreated controls; phytotoxicity 100%: maximum damage). The protective action, expressed in %, is found from the difference between the phytotoxicity caused by application of the herbicide alone and the phytotoxicity occurring when herbicide and safener are applied.

As active ingredients there are used the herbicide HE-7 employed in Example B6 and the safener of formula I N-(5,7-dimethyl-1,2,4-triazolo[1,5-a]pyrimidin-2-ylsulfonyl)-3-aminothiophene-2-carboxylic acid ethyl ester (S-5). The results are shown in Table 11.

TABLE 11

| HE-7 appl. rate [kg/ha] | 0.5 | | | 0.25 | | |
|---|---|---|---|---|---|---|
| S-5 or S-2 application rate [kg/ha] | 0.5 | 0.25 | 0.125 | 0.5 | 0.25 | 0.125 |
| S-5, protec. action in %: | 37 | 25 | 25 | 25 | 25 | 25 |
| S-2, protec. action in %: | 25 | 25 | 25 | 37 | 25 | 50 |

FORMULATION EXAMPLES

The abbreviations used to denote the herbicides and safeners in the Formulation Examples correspond to those used in the Biological Examples above.

FORMULATION EXAMPLES FOR HERBICIDE/SAFENER MIXTURES

| F1 Wettable powder | (a) | (b) | (c) | (d) |
|---|---|---|---|---|
| herbicide HE-1 | 10% | 20% | 5% | 30% |
| safener S-1 | 10% | 40% | 15% | 30% |
| sodium lignosulfonate | 5% | 5% | 5% | 5% |
| sodium lauryl sulfate | 3% | — | 3% | — |
| sodium diisobutyl-naphthalenesulfonate | — | 6% | — | 6% |
| octylphenol polyethylene glycol ether (7-8 moles of ethylene oxide) | — | 2% | — | 2% |
| highly dispersed silicic acid | 5% | 27% | 5% | 27% |
| kaolin | 67% | — | 67% | — |

The active ingredient mixture is thoroughly mixed with the adjuvants and the mixture is thoroughly ground in a suitable mill, affording wettable powders which can be diluted with water to give suspensions of the desired concentration.

| F2 Emulsifiable concentrate | (a) | (b) | (c) |
|---|---|---|---|
| herbicide HE-7 | 5% | 5% | 12% |
| safener S-1 | 5% | 20% | 13% |
| octylphenol polyethylene glycol ether (4-5 moles of ethylene oxide) | 3% | 3% | 3% |
| calcium dodecylbenzenesulfonate | 3% | 3% | 2% |
| castor oil polyglycol ether (36 moles of ethylene oxide) | 4% | 4% | 4% |
| cyclohexanone | 30% | 30% | 31% |
| xylene mixture | 50% | 35% | 35% |

Emulsions of any required concentration can be obtained from this concentrate by dilution with water.

| F3 Dusts | (a) | (b) | (c) | (d) |
|---|---|---|---|---|
| herbicide HE-4 | 2% | 4% | 2% | 4% |
| safener S-1 | 3% | 4% | 4% | 8% |
| talcum | 95% | — | 94% | — |
| kaolin | — | 92% | — | 88% |

Ready-for-use dusts are obtained by mixing the active ingredient mixture with the carrier and grinding the mixture in a suitable mill.

| F4 Extruder granulate | (a) | (b) | (c) |
|---|---|---|---|
| herbicide HE-4 | 5% | 3% | 5% |
| safener S-1 | 5% | 7% | 15% |
| sodium lignosulfonate | 2% | 2% | 2% |
| carboxymethylcellulose | 1% | 1% | 1% |
| kaolin | 87% | 87% | 77% |

The active ingredient mixture is mixed and ground with the adjuvants, and the mixture is moistened with water. The mixture is extruded and then dried in a stream of air.

| F5 Coated granulate | (a) | (b) |
|---|---|---|
| herbicide HE-4 | 1.5% | 3% |
| safener S-1 | 1.5% | 5% |
| polyethylene glycol (mol. wt. 200) | 3% | 3% |
| kaolin | 94% | 89% |

The finely ground active ingredient mixture is uniformly applied, in a mixer, to the kaolin moistened with polyethylene glycol. Non-dusty coated granulates are obtained in this manner.

| F6 Suspension concentrate | (a) | (b) |
|---|---|---|
| herbicide HE-4 | 20% | 20% |
| safener S-1 | 20% | 40% |
| ethylene glycol | 10% | 10% |
| nonylphenol polyethylene glycol ether (15 moles of ethylene oxide) | 6% | 6% |
| sodium lignosulfonate | 10% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 12% |

The finely ground active ingredient mixture is intimately mixed with the adjuvants, giving a suspension concentrate from which suspensions of any desired concentration can be obtained by dilution with water.

FORMULATION EXAMPLES FOR ANTIDOTES OF FORMULA I (THROUGHOUT, PERCENTAGES ARE BY WEIGHT)

| Fa-1 Wettable powder | (a) | (b) | (c) |
|---|---|---|---|
| compound of Table 1 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Fa-2 Emulsifiable concentrate | |
|---|---|
| compound of Table 1 | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| Fa-3 Dusts | (a) | (b) |
|---|---|---|
| compound of Table 1 | 5% | 8% |

-continued

| Fa-3 Dusts | (a) | (b) |
|---|---|---|
| talcum | 95% | — |
| kaolin | — | 92% |

Ready-for-use dusts are obtained by mixing the active ingredient with the carrier and grinding the mixture in a suitable mill.

| Fa-4 Extruder granulate | |
|---|---|
| compound of Table 1 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| Fa-5 Coated granulate | |
|---|---|
| compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| Fa-6 Suspension concentrate | |
|---|---|
| compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

What is claimed is:

1. A method of protecting soybeans or cereals from the harmful effects of herbicidal sulfonylureas of the formula II

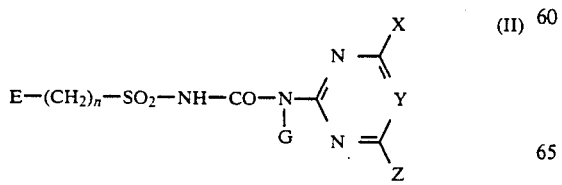

wherein E is one of the structural elements

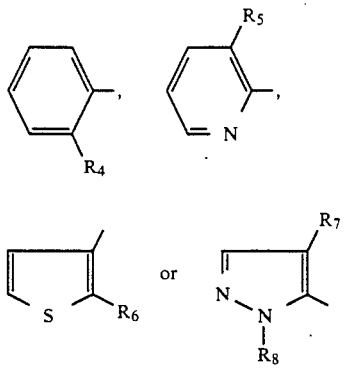

n is the number 0 or 1,
G is hydrogen or methyl,
X is methoxy, ethoxy, difluoromethoxy, methyl or chlorine,
Y is CH or N,
Z is methoxy, methyl, difluoromethoxy, cyclopropyl or methylamino,
$R_4$ is $C_2$-$C_5$alkoxyalkoxy, $C_1$-$C_4$haloalkoxy, $C_1$-$C_4$haloalkylthio, $C_2$-$C_4$haloalkenyl, chlorine or $C_1$-$C_4$alkoxycarbonyl,
$R_5$ is trifluoromethyl or di($C_1$-$C_4$alkyl)carbamoyl,
$R_6$ is $C_1$-$C_4$alkoxycarbonyl,
$R_7$ is $C_1$-$C_4$alkoxycarbonyl, and
$R_8$ is $C_1$-$C_4$alkyl,
chloroacetanilides of formula III

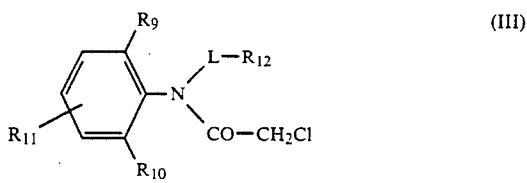

wherein
L is a $C_1$-$C_5$alkylene bridge,
each of $R_9$, $R_{10}$ and $R_{11}$, independently of the others, is hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R_{12}$ is hydrogen, $C_1$-$C_4$alkoxy, —COOH, $C_1$-$C_4$alkoxycarbonyl, —CONH$_2$, $C_1$-$C_4$alkylcarbamoyl, di—$C_1$-$C_4$alkylcarbamoyl, cyano, $C_1$-$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl or unsubstituted or substituted tetrahydrofuryl,
or the structural element —L—$R_{12}$ is a $C_1$-$C_4$alkylene bridge substituted by two $C_1$-$C_3$alkoxy groups or is 5-methyl-1,3,4-oxadiazol-2-yl,
aryloxyphenoxypropionic acid derivatives of formula IV

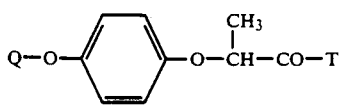

(IV)

wherein
Q is a radical

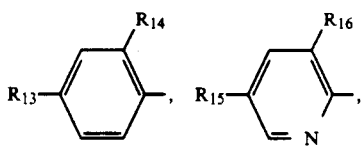

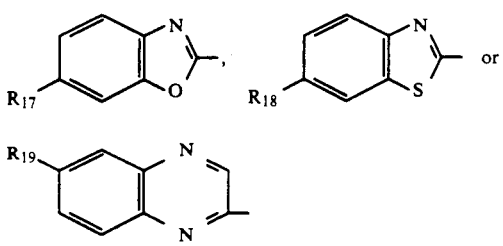

and

T is —NR$_{20}$R$_{21}$, —N(CN)R$_{22}$, —OR$_{23}$, SR$_{24}$ or —O—N=CR$_{25}$R$_{26}$, wherein R$_{13}$ and R$_{15}$ are halogen or trifluoromethyl, R$_{14}$, R$_{16}$, R$_{17}$, R$_{18}$ and R$_{19}$ are hydrogen or halogen, each of R$_{20}$ and R$_{21}$, independently of the other, is hydrogen, C$_1$-C$_8$alkoxy, C$_1$-C$_8$alkyl, phenyl or benzyl, or R$_{20}$ and R$_{21}$ together with the nitrogen atom carrying them form a 5- or 6-membered saturated nitrogen heterocycle that may be interrupted by an oxygen or a sulfur atom, R$_{22}$ is C$_1$-C$_4$alkyl, C$_3$-C$_4$alkenyl, C$_3$-C$_4$alkynyl or C$_2$-C$_4$alkoxyalkyl, R$_{23}$ is hydrogen or the equivalent of an alkali metal, alkaline earth metal, copper or iron ion; a quaternary C$_1$-C$_4$alkylammonium or C$_1$-C$_4$hydroxyalkylammonium radical; a C$_1$-C$_9$alkyl radical which is unsubstituted or mono- or poly-substituted by amino, halogen, hydroxy, cyano, nitro, phenyl, C$_1$-C$_4$alkoxy, polyethoxy having from 2 to 6 ethylene oxide units, —COOR$_{27}$, —COSR$_{28}$, —CONH$_2$, —CON(C$_1$-C$_4$alkoxy)—C$_1$-C$_4$alkyl, —CO—N-di-C$_1$-C$_4$alkyl, CONH—C$_1$-C$_4$alkyl, —N(C$_1$-C$_4$alkoxy)—C$_1$-C$_4$alkyl or by di-C$_1$-C$_4$alkylamino; a C$_3$-C$_9$alkenyl radical which is unsubstituted or substituted by halogen or by C$_1$-C$_4$alkoxy; a C$_3$-C$_9$alkynyl radical which is unsubstituted or substituted by halogen or by C$_1$-C$_4$alkoxy; C$_3$-C$_9$cycloalkyl; or phenyl which is unsubstituted or substituted by cyano, C$_1$-C$_4$alkyl, C$_1$-C$_4$alkoxy, acetyl, —COOR$_{29}$, COSR$_{30}$, —CONH$_2$, —CON(-C$_1$-C$_4$alkoxy)—C$_1$-C$_4$alkyl, —CO—N—di—C$_1$-C$_4$alkyl or by —CONH—C$_1$-C$_4$alkyl, each of R$_{25}$ and R$_{26}$, independently of the other, is C$_1$-C$_4$alkyl, or R$_{25}$ and R$_{26}$ together form a 3- to 6-membered alkylene chain, and each of R$_{27}$, R$_{28}$, R$_{29}$ and R$_{30}$, independently of the others, is hydrogen, C$_1$-C$_6$alkyl, C$_1$-C$_6$-haloalkyl, C$_2$-C$_6$alkoxyalkyl, C$_3$-C$_6$alkenyl, C$_3$-C$_6$haloalkyl, C$_3$-C$_6$alkynyl or C$_3$-C$_6$haloalkynyl, or N-benzoyl-N-phenylalanine derivatives of formula V

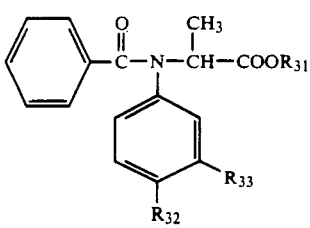

wherein

R$_{31}$ is hydrogen or C$_1$-C$_4$alkyl and each of R$_{32}$ and R$_{33}$, independently of the other, is fluorine or chlorine, which comprises treating the cultivated plant or the locus thereof with up to 2 Kg/ha of a compound of the formula I

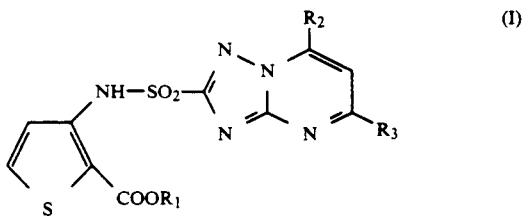

wherein

R$_1$ is C$_1$-C$_6$alkyl or C$_3$-C$_6$cycloalkyl, and each of R$_2$ and R$_3$, independently of the other, is hydrogen, C$_1$-C$_3$alkyl, trifluoromethyl or cyclopropyl, with the proviso that only one of the symbols R$_2$ and R$_3$ may be hydrogen.

2. The method of claim 1, wherein each of R$^2$ and R$^3$, independently of the other, is C$_1$-C$_3$alkyl or cyclopropyl.

3. The method of claim 1, wherein one of the symbols R$^2$ and R$^3$ is methyl and the other is cyclopropyl.

4. The method of claim 1, wherein wherein R$^1$ is methyl.

5. The method of claim 1, wherein N-(5,7-dimethyl-1,2,4-triazolo-[1,5-a]pyrimidin-2-ylsulfonyl)-3-aminothiophene-2-carboxylic acid methyl ester of formula Ia

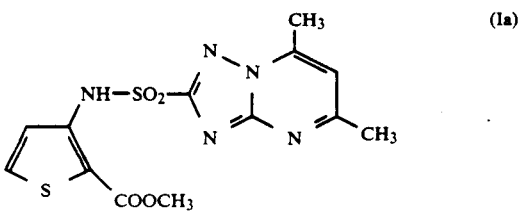

is used as antidote.

6. The method of claim 1, for the protection against the phytotoxic effects caused by a herbicidal sulfonylurea derivative of formula II

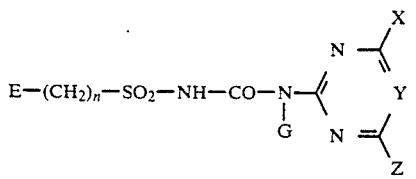 (II)

wherein E is one of the structural elements

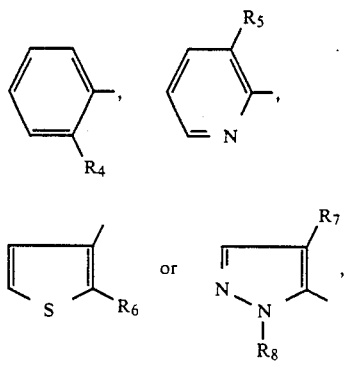

n is the number 0 or 1, G is hydrogen or methyl, X is methoxy, ethoxy, difluoromethoxy, methyl or chlorine, Y is CH or N, Z is methoxy, methyl, difluoromethoxy, cyclopropyl or methylamino, $R^4$ is $C_2$-$C_5$alkoxyalkoxy, $C_1$-$C_4$haloalkoxy, $C_1$-$C_4$haloalkylthio, $C_2$-$C_4$haloalkenyl, chlorine or $C_1$-$C_4$alkoxycarbonyl, $R^5$ is trifluoromethyl or di($C_1$-$C_4$alkyl)carbamoyl, $R^6$ is $C_1$-$C_4$alkoxycarbonyl, $R^7$ is $C_1$-$C_4$alkoxycarbonyl, and $R^8$ is $C_1$-$C_4$alkyl.

7. The method of claim 1, for the protection against the phytotoxic effects caused by a herbicidal chloroacetanilide of formula III

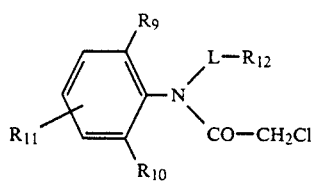 (III)

wherein L is a $C_1$-$C_5$alkylene bridge, each of $R^9$, $R^{10}$ and $R^{11}$ independently of the others, is hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R^{12}$ is hydrogen, $C_1$-$C_4$alkoxy, —COOH, $C_1$-$C_4$alkoxyalkyl, —CONH$_2$, $C_1$-$C_4$alkylcarbamoyl, di—$C_1$-$C_4$alkylcarbamoyl, cyano, $C_1$-$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2yl, unsubstituted or substituted 1,2,4-triazol-3-yl, unsubstituted or substituted dioxolanyl, unsubstituted or substituted dioxanyl or unsubstituted or substituted tetrahydrofuryl, or the structural element —L—$R^{12}$ is a $C_1$-$C_4$alkylene bridge substituted by two $C_1$-$C_3$alkoxy groups or is 5-methyl-1,3,4-oxadiazol-2-yl.

8. The method of claim 1, for the protection against the phytotoxic effects caused by a herbicidal aryloxyphenoxypropionic acid derivative of formula IV

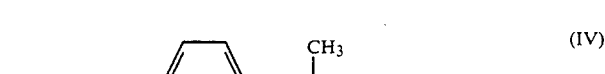 (IV)

wherein Q is a radical

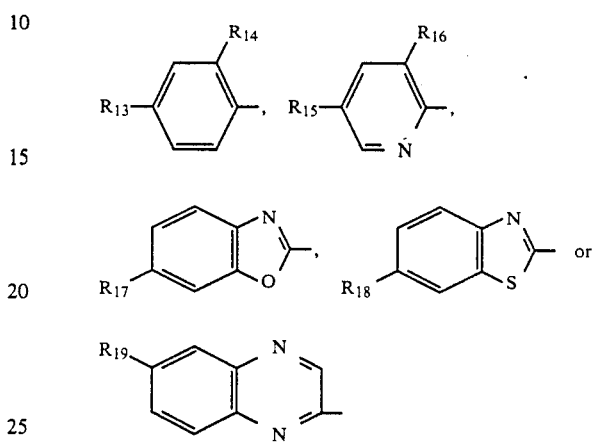

and T is —NR$^{20}$R$^{21}$, —N(CN)R$^{22}$, —OR$^{23}$, SR$^{24}$ or —O—N=CR$^{25}$R$^{26}$, wherein R$^{13}$ and R$^{15}$ are halogen or trifluoromethyl, R$^{14}$, R$^{16}$, R$^{17}$, R$^{18}$ and R$^{19}$ are hydrogen or halogen, each of R$^{20}$ and R$^{21}$ independently of the other, is hydrogen, $C_1$-$C_8$alkoxy, $C_1$-$C_8$alkyl, phenyl or benzyl, or R$^{20}$ and R$^{21}$ together with the nitrogen atom carrying them form a 5- or 6-membered saturated nitrogen heterocycle that may be interrupted by an oxygen or a sulfur atom, R$^{22}$ is $C_1$-$C_4$alkyl, $C_3$-$C_4$alkenyl, $C_3$-$C_4$alkynyl or $C_2$-$C_4$alkoxyalkyl, R$^{23}$ is hydrogen or the equivalent of an alkali metal, alkaline earth metal, copper or iron ion; a quaternary $C_1$-$C_4$alkylammonium or $C_1$-$C_4$hydroxyalkylammonium radical; a $C_1$-$C_9$alkyl radical which is unsubstituted or mono- or poly-substituted by amino, halogen, hydroxy, cyano, nitro, phenyl, $C_1$-$C_4$alkoxy, polyethoxy having from 2 to 6 ethylene oxide units, —COOR$^{27}$, —COSR$^{28}$, —CONH$_2$, —CON($C_1$-$C_4$alkoxy)—$C_1$-$C_4$alkyl, —CO—N—di—$C_1$-$C_4$alkyl, CONH-$C_1$-$C_4$alkyl, —N(-$C_1$-$C_4$alkoxy)—$C_1$-$C_4$alkyl or by di—$C_1$-$C_4$alkylamino; a $C_3$-$C_9$alkenyl radical which is unsubstituted or substituted by halogen or by $C_1$-$C_4$alkoxy; a $C_3$-$C_9$alkynyl radical which is unsubstituted or substituted by halogen or by $C_1$-$C_4$alkoxy; $C_3$-$C_9$cycloalkyl; or phenyl which is unsubstituted or substituted by cyano, $C_1$-$C_4$alkyl, $C_1$-$C_4$alkoxy, acetyl, —COOR$^{29}$, COSR$^{30}$, —CONH$_2$, —CON($C_1$-$C_4$alkoxy)—$C_1$-$C_4$alkyl, —CO—N-di-$C_1$-$C_4$alkyl or by —CONH—$C_1$-$C_4$alkyl, each of R$^{25}$ and R$^{26}$ independently of the other, is $C_1$-$C_4$alkyl, or R$^{25}$ and R$^{26}$ together form a 3- to 6-membered alkylene chain, and each of R$^{27}$, R$^{28}$, R$^{29}$ and R$^{30}$ independently of the others, is hydrogen, $C_1$-$C_6$alkyl, $C_1$-$C_6$haloalkyl, $C_2$-$C_6$alkoxyalkyl, $C_3$-$C_6$alkenyl, $C_3$-$C_6$haloalkyl, $C_3$-$C_6$alkynyl or $C_3$-$C_6$haloalkynyl.

9. The method of claim 1, for the protection against the phytotoxic effects caused by a herbicidal N-benzoyl-N-phenylalanine derivative of formula V

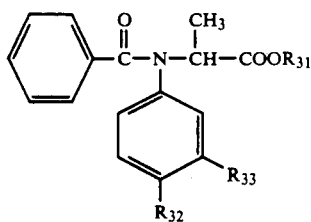

(V)

wherein $R^{31}$ is hydrogen or $C_1$-$C_4$alkyl and each of $R^{32}$ and $R^{33}$ independently of the other, is fluorine or chlorine.

10. A method of protecting soybeans or cereals from the harmful effects of herbicidal sulfonylureas of the formula II

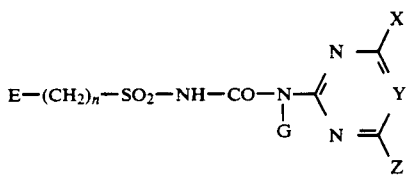

(II)

wherein E is one of the structural elements

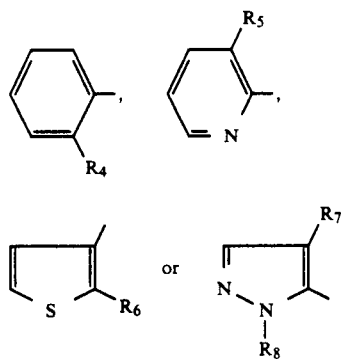

n is the number 0 or 1,
G is hydrogen or methyl,
X is methoxy, ethoxy, difluoromethoxy, methyl or chlorine,
Y is CH or N,
Z is methoxy, methyl, difluoromethoxy, cyclopropyl or methylamino,
$R_4$ is $C_2$-$C_5$alkoxyalkoxy, $C_1$-$C_4$haloalkoxy, $C_1$-$C_4$-haloalkylthio, $C_2$-$C_4$haloalkenyl, chlorine or $C_1$-$C_4$alkoxycarbonyl,
$R_5$ is trifluoromethyl or di($C_1$-$C_4$alkyl)carbamoyl,
$R_6$ is $C_1$-$C_4$alkoxycarbonyl,
$R_7$ is $C_1$-$C_4$alkoxycarbonyl, and
$R_8$ is $C_1$-$C_4$alkyl,
chloroacetanilides of formula III

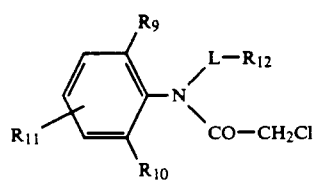

(III)

wherein
L is a $C_1$-$C_5$alkylene bridge, each of $R_9$, $R_{10}$ and $R_{11}$, independently of the others, is hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R_{12}$ is hydrogen, $C_1$-$C_4$alkoxy, —COOH, $C_1$-$C_4$alkoxycarbonyl, —CONH$_2$, $C_1$-$C_4$alkylcarbamoyl, di—$C_1$-$C_4$alkylcarbamoyl, cyano, $C_1$-$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl or unsubstituted or substituted tetrahydrofuryl,
or the structural element -L-$R_{12}$ is a $C_1$-$C_4$alkylene bridge substituted by two $C_1$-$C_3$alkoxy groups or is 5-methyl-1,3,4-oxadiazol-2-yl,
aryloxyphenoxypropionic acid derivatives of formula IV

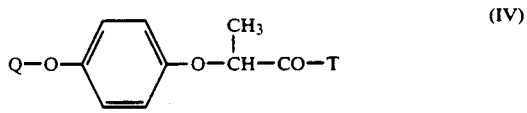

(IV)

wherein
Q is a radical

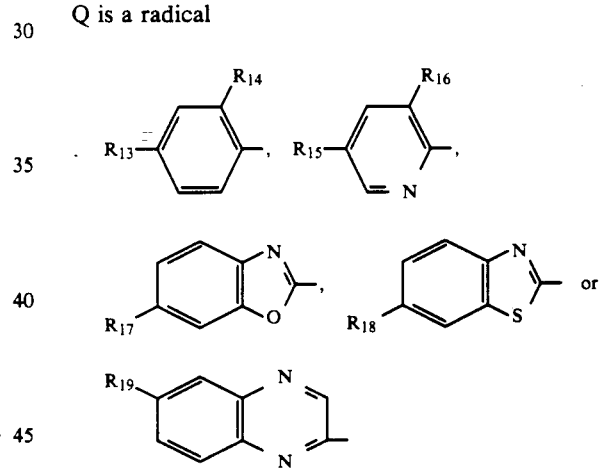

and
T is —NR$_{20}$R$_{21}$, —N(CN)R$_{22}$, —OR$_{23}$, SR$_{24}$ or —O—N=CR$_{25}$R$_{26}$, wherein
$R_{13}$ and $R_{15}$ are halogen or trifluoromethyl,
$R_{14}$, $R_{16}$, $R_{17}$, $R_{18}$ and $R_{19}$ are hydrogen or halogen,
each of $R_{20}$ and $R_{21}$, independently of the other, is hydrogen, $C_1$-$C_8$alkoxy, $C_1$-$C_8$alkyl, phenyl or benzyl, or
$R_{20}$ and $R_{21}$ together with the nitrogen atom carrying them form a 5- or 6-membered saturated nitrogen heterocycle that may be interrupted by an oxygen or a sulfur atom,
$R_{22}$ is $C_1$-$C_4$alkyl, $C_3$-$C_4$alkyenyl, $C_3$-$C_4$alkynyl or $C_2$-$C_4$alkoxyalkyl,
$R_{23}$ is hydrogen or the equivalent of an alkali metal, alkaline earth metal, copper or iron ion; a quaternary $C_1$-$C_4$alkylammonium or $C_1$-$C_4$hydroxyalkylammonium radical; a $C_1$-$C_9$alkyl radical which is unsubstituted or mono- or poly-substituted by amino, halogen, hydroxy, cyano, nitro, phenyl, $C_1$-$C_4$alkoxy, polyethoxy having from 2 to 6 ethylene oxide units, —COOR$_{27}$, —COSR$_{28}$, —CONH$_2$, —CON(C$_1$-C$_4$alkoxy)—C$_1$-C$_4$alkyl, —CO—N—di—C$_1$-C$_4$alkyl, CONH—C$_1$-C$_4$alkyl, —N(C$_1$-C$_4$alkoxy)—C$_1$-C$_4$alkyl or by di—C$_1$-C$_4$alkylamino; a C$_3$-C$_9$alkenyl radical which is unsubstituted or substituted by halogen or by C$_1$-C$_4$alkoxy; a C$_3$-C$_9$alkynyl radical which is unsubstituted or substituted by halogen or by C$_1$-C$_4$alkoxy; C$_3$-C$_9$cycloalkyl; or phenyl which is unsubstituted or substituted by cyano, C$_1$-C$_4$alkyl, C$_1$-C$_4$alkoxy, acetyl, —COOR$_{29}$, COSR$_{30}$, —CONH$_2$, —CON(-C$_1$-C$_4$alkoxy)—C$_1$-C$_4$alkyl, —CO—N—di—C$_1$-C$_4$alkyl or by —CONH—C$_1$-C$_4$alkyl, each of R$_{25}$ and R$_{26}$, independently of the other, is C$_1$-C$_4$alkyl, or R$_{25}$ and R$_{26}$ together form a 3- to 6-membered alkylene chain, and each of R$_{27}$, R$_{28}$, R$_{29}$ and R$_{30}$, independently of the others, is hydrogen, C$_1$-C$_6$alkyl, C$_1$-C$_6$-haloalkyl, C$_2$-C$_6$alkoxyalkyl, C$_3$-C$_6$alkenyl, C$_3$-C$_6$haloalkenyl, C$_3$-C$_6$alkynyl or C$_3$-C$_6$haloalkynyl, or N-benzoyl-N-phenylalanine derivatives of formula V

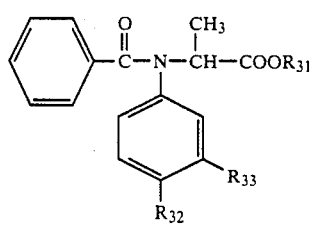

wherein

R$_{31}$ is hydrogen or C$_1$-C$_4$alkyl and each of R$_{32}$ and R$_{33}$, independently of the other, is fluorine or chlorine, which method comprises treating the seeds the soybean or the cereal with an antidotally effective amount of a compound of the formula I

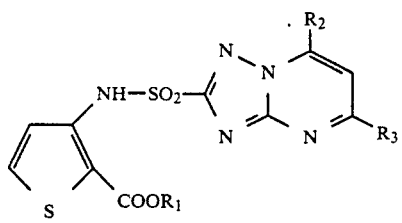

wherein

R$_1$ is C$_1$-C$_6$alkyl or C$_3$-C$_6$cycloalkyl, and each of R$_2$ and R$_3$, independently of the other, is hydrogen, C$_1$-C$_3$alkyl, trifluoromethyl or cyclopropyl, with the proviso that only one of the symbols R$_2$ and R$_3$ may be hydrogen.

11. A composition for protecting soybeans or cereals from the harmful effects of herbicidal sulfonylureas, comprising a herbicidal sulfonylurea of the formula II

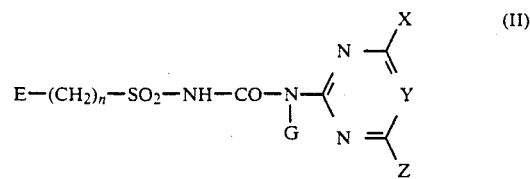

wherein E is one of the structural elements

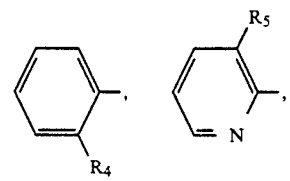

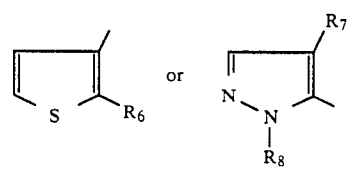

n is the number 0 or 1,

G is hydrogen or methyl,

X is methoxy, ethoxy, difluoromethoxy, methyl or chlorine,

Y is CH or N,

Z is methoxy, methyl, difluoromethoxy, cyclopropyl or methylamino,

R$_4$ is C$_2$-C$_5$alkoxyalkoxy, C$_1$-C$_4$haloalkoxy, C$_1$-C$_4$haloalkylthio, C$_2$-C$_4$haloalkenyl, chlorine or C$_1$-C$_4$alkoxycarbonyl, R$_5$ is trifluoromethyl or di(C$_1$-C$_4$alkyl)carbamoyl, R$_6$ is C$_1$-C$_4$alkoxycarbonyl, R$_7$ is C$_1$-C$_4$alkoxycarbonyl, and R$_8$ is C$_1$-C$_4$alkyl, chloroacetanilides of formula III

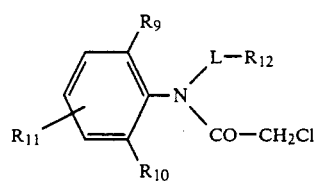

wherein

L is a C$_1$-C$_5$alkylene bridge, each of R$_9$, R$_{10}$ and R$_{11}$, independently of the others, is hydrogen, halogen, C$_1$-C$_4$alkyl, C$_1$-C$_4$alkoxy, C$_1$-C$_4$haloalkyl, C$_2$-C$_5$alkoxyalkyl or C$_2$-C$_5$alkylthioalkyl, and R$_{12}$ is hydrogen, C$_1$-C$_4$alkoxy, —COOH, C$_1$-C$_4$alkoxycarbonyl, —CONH$_2$, C$_1$-C$_4$alkylcarbamoyl, di—C$_1$-C$_4$alkylcarbamoyl, cyano, C$_1$-C$_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl or unsubstituted or substituted tetrahydrofuryl, or the structural element —L—R$_{12}$ is a C$_1$-C$_4$alkylene bridge substituted by two C$_1$-C$_3$alkoxy groups or is 5-methyl-1,3,4-oxadiazol-2-yl, aryloxyphenoxypropionic acid derivatives of formula IV

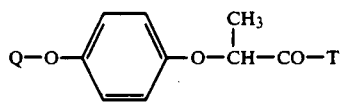

wherein

Q is a radical

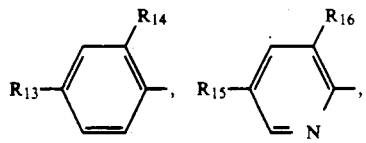

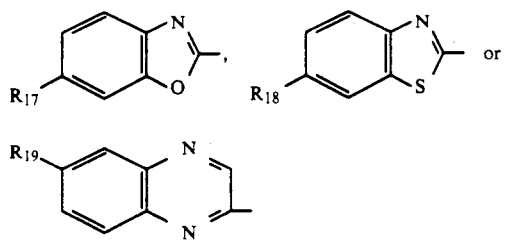

and

T is —NR$_{20}$R$_{21}$, —N(CN)R$_{22}$, —OR$_{23}$, SR$_{24}$ or —O—N=CR$_{25}$R$_{26}$, wherein R$_{13}$ and R$_{15}$ are halogen or trifluoromethyl, R$_{14}$, R$_{16}$, R$_{17}$, R$_{18}$ and R$_{19}$ are hydrogen or halogen, each of R$_{20}$ and R$_{21}$, independently of the other, is hydrogen, C$_1$-C$_8$alkoxy, C$_1$-C$_8$alkyl, phenyl or benzyl, or R$_{20}$ and R$_{21}$ together with the nitrogen atom carrying them form a 5- or 6-membered saturated nitrogen heterocycle that may be interrupted by an oxygen or a sulfur atom, R$_{22}$ is C$_1$-C$_4$alkyl, C$_3$-C$_4$alkenyl, C$_3$-C$_4$alkynyl or C$_2$-C$_4$alkoxyalkyl, R$_{23}$ is hydrogen or the equivalent of an alkali metal, alkaline earth metal, copper or iron ion; a quaternary C$_1$-C$_4$alkylammonium or C$_1$-C$_4$hydroxyalkylammonium radical; a C$_1$-C$_9$alkyl radical which is unsubstituted or mono- or poly-substituted by amino, halogen, hydroxy, cyano, nitro, phenyl, C$_1$-C$_4$alkoxy, polyethoxy having from 2 to 6 ethylene oxide units, —COOR$_{27}$, —COSR$_{28}$, —CONH$_2$, —CON(C$_1$-C$_4$alkoxy)—C$_1$-C$_4$alkyl, —CO—N—di—C$_1$-C$_4$alkyl, CONH—C$_1$-C$_4$alkyl, —N(C$_1$-C$_4$alkoxy)—C$_1$-C$_4$alkyl or by di—C$_1$-C$_4$alkylamino; a C$_3$-C$_9$alkenyl radical which is unsubstituted or substituted by halogen or by C$_1$-C$_4$alkoxy; a C$_3$-C$_9$alkynyl radical which is unsubstituted or substituted by halogen or by C$_1$-C$_4$alkoxy; C$_3$-C$_9$cycloalkyl; or phenyl which is unsubstituted or substituted by cyano, C$_1$-C$_4$alkyl, C$_1$-C$_4$alkoxy, acetyl, —COOR$_{29}$, COSR$_{30}$, —CONH$_2$, —CON(-C$_1$-C$_4$alkoxy)—C$_1$-C$_4$alkyl, —CO—N—di—C$_1$-C$_4$alkyl or by —CONH—C$_1$-C$_4$alkyl, each of R$_{25}$ and R$_{26}$, indenpendently of the other, is C$_1$-C$_4$alkyl, or R$_{25}$ and R$_{26}$ together form a 3- to 6-membered alkylene chain, and each of R$_{27}$, R$_{28}$, R$_{29}$ and R$_{30}$, independently of the others, is hydrogen, C$_1$-C$_6$alkyl, C$_1$-C$_6$-haloalkyl, C$_2$-C$_6$alkoxyalkyl, C$_3$-C$_6$alkenyl, C$_3$-C$_6$haloalkyl, C$_3$-C$_6$alkynyl or C$_3$-C$_6$haloalkynyl, or N-benzoyl-N-phenylalanine derivatives of formula V

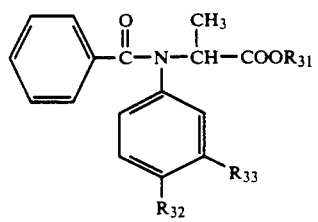

wherein

R$_{31}$ is hydrogen or C$_1$-C$_4$alkyl and each of R$_{32}$ and R$_{33}$, independently of the other, is fluorine or chlorine, together with an antidotely effective amount of a compound of the formula I

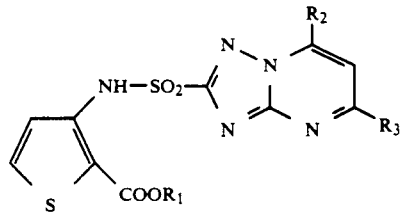

wherein

R$_1$ is C$_1$-C$_6$alkyl or C$_3$-C$_6$cycloalkyl, and each of R$_2$ and R$_3$, independently of the other, is hydrogen, C$_1$-C$_3$alkyl, trifluoromethyl or cyclopropyl, with the proviso that only one of the symbols R$_2$ and R$_3$ may be hydrogen.

12. A herbicidal composition of claim 11, wherein the herbicide is a sulfonylurea derivative of formula II

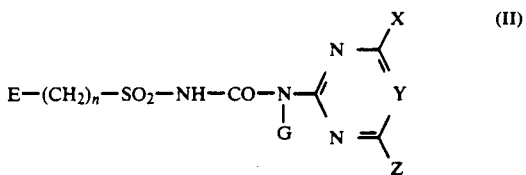

wherein E is one of the structural elements

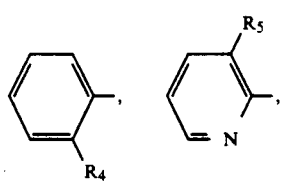

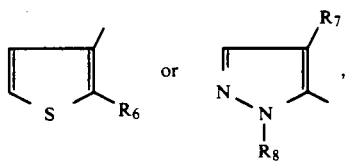

n is the number 0 or 1, G is hydrogen or methyl, X is methoxy, ethoxy, difluoromethoxy, methyl or chlorine, Y is CH or N, Z is methoxy, methyl, difluoromethoxy, cyclopropyl or methylamino, $R^4$ is $C_2$-$C_5$alkoxyalkoxy, $C_1$-$C_4$haloalkoxy, $C_1$-$C_4$haloalkythio, $C_2$-$C_4$haloalkenyl, chlorine or $C_1$-$C_4$alkoxycarbonyl, $R^5$ is trifluoromethyl or di($C_1$-$C_4$alkyl)carbamoyl, $R^6$ is $C_1$-$C_4$alkoxycarbonyl, $R^7$ is $C_1$-$C_4$alkoxycarbonyl, and $R^8$ is $C_1$-$C_4$alkyl.

13. A herbicidal composition of claim 11, wherein the herbicide is a chloroacetanilide of formula III

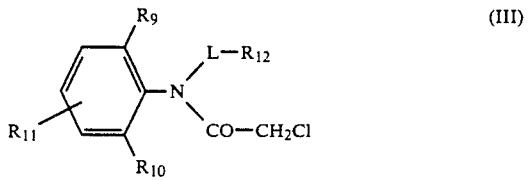

wherein L is a $C_1$-$C_5$alkylene bridge, each of $R^9$, $R^{10}$ and $R^{11}$ independently of the others, is hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R^{12}$ is hydrogen, $C_1$-$C_4$alkoxy, —COOH, $C_1$-$C_4$alkoxycarbonyl, —CONH$_2$, $C_1$-$C_4$alkylcarbamoyl, di—$C_1$-$C_4$alkylcarbamoyl, cyano, $C_1$-$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl or unsubstituted or substituted tetrahydrofuryl, or the structural element —L—$R^{12}$ is a $C_1$-$C_4$alkylene bridge substituted by two $C_1$-$C_3$alkoxy groups or is 5-methyl-1,3,4-oxadiazol-2-yl.

14. A herbicidal composition of claim 11, wherein the herbicide is a aryloxyphenoxypropionic acid derivative of formula IV

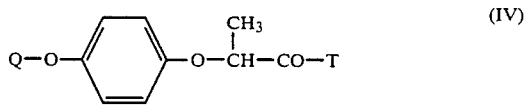

wherein Q is a radical

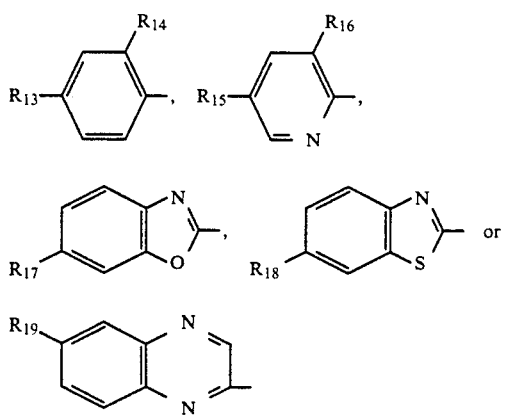

and T is —NR$^{20}$R$^{21}$, —N(CN)R$^{22}$, —OR$^{23}$, SR$^{24}$ or —O—N=CR$^{25}$R$^{26}$, wherein R$^{13}$ and R$^{15}$ are halogen or trifluoromethyl, R$^{14}$, R$^{16}$, R$^{17}$, R$^{18}$ and R$^{19}$ are hydrogen or halogen, each of R$^{20}$ and R$^{21}$ independently of the other, is hydrogen, $C_1$-$C_8$alkoxy, $C_1$-$C_8$alkyl, phenyl or benzyl, or R$^{20}$ and R$^{21}$ together with the nitrogen atom carrying them form a 5- or 6-membered saturated nitrogen heterocycle that may be interrupted by an oxygen or a sulfur atom, R$^{22}$ is $C_1$-$C_4$alkyl, $C_3$-$C_4$alkenyl, $C_3$-$C_4$alkynyl or $C_2$-$C_4$alkoxyalkyl, R$^{23}$ is hydrogen or the equivalent of an alkali metal, alkaline earth metal, copper or iron ion; a quaternary $C_1$-$C_4$alkylammonium or $C_1$-$C_4$hydroxyalkylammonium radical; a $C_1$-$C_9$alkyl radical which is unsubstituted or mono- or poly-substituted by amino, halogen, hydroxy, cyano, nitro, phenyl, $C_1$-$C_4$alkoxy, polyethoxy having from 2 to 6 ethylene oxide units, —COOR$^{27}$, —COSR$^{28}$, —CONH$_2$, —CON($C_1$-$C_4$alkoxy)—$C_1$-$C_4$alkyl, —CO—N—di—$C_1$-$C_4$alkyl, CONH—$C_1$-$C_4$alkyl, —N($C_1$-$C_4$alkoxy)—$C_1$-$C_4$alkyl or by di—$C_1$-$C_4$alkylamino; a $C_3$-$C_9$alkenyl radical which is unsubstituted or substituted by halogen or by $C_1$-$C_4$alkoxy; a $C_3$-$C_9$alkynyl radical which is unsubstituted or substituted by halogen or by $C_1$-$C_4$alkoxy; $C_3$-$C_9$cycloalkyl; or phenyl which is unsubstituted or substituted by cyano, $C_1$-$C_4$alkyl, $C_1$-$C_4$alkoxy, acetyl, —COOR$^{29}$, COSR$^{30}$, —CONH$_2$, —CON($C_1$-$C_4$alkoxy)—$C_1$-$C_4$alkyl, —CO—N—di—$C_1$-$C_4$alkyl or by —CONH—$C_1$-$C_4$alkyl, each of R$^{25}$ and R$^{26}$ independently of the other, is $C_1$-$C_4$alkyl, or R$^{25}$ and R$^{26}$ together form a 3- to 6-membered alkylene chain, and each of R$^{27}$, R$^{28}$, R$^{29}$ and R$^{30}$ independently of the others, is hydrogen, $C_1$-$C_6$alkyl, $C_1$-$C_6$haloalkyl, $C_2$-$C_6$alkoxyalkyl, $C_3$-$C_6$alkenyl, $C_3$-$C_6$haloalkenyl, $C_3$-$C_6$alkynyl or $C_3$-$C_6$haloalkynyl.

15. A herbicidal composition of claim 11, wherein the herbicide is a N-benzoyl-N-phenylalanine derivative of formula V

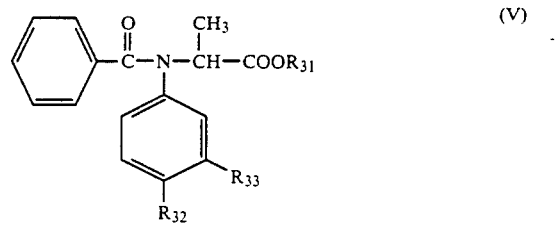

wherein R$^{31}$ is hydrogen or $C_1$-$C_4$alkyl and each of R$^{32}$ and R$^{33}$ independently of the other, is fluorine or chlorine.

16. A compound of formula I'

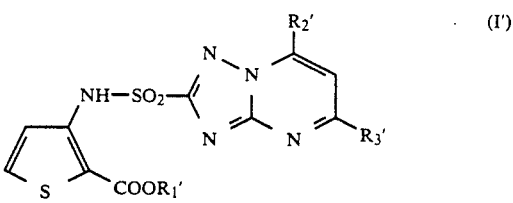

wherein R$^{1'}$ is $C_1$-$C_6$alkyl or $C_3$-$C_6$cycloalkyl, and each of R$^{2'}$ and R$^{3'}$, independently of the other, is hydrogen, $C_1$-$C_3$alkyl, trifluoromethyl or cyclopropyl, with the proviso that at least one of the symbols R$^{2'}$ or R$^{3'}$ is cyclopropyl.

17. A compound of claim 16, wherein one of the symbols R$^{2'}$ or R$^{3'}$ is cyclopropyl and the other is methyl.

18. A compound of claim 16, wherein $R^{1'}$ is methyl.

19. A compound of claim 16, wherein $R^{1'}$ is methyl and one of the symbols $R^{2'}$ or $R^{3'}$ is cyclopropyl and the other is methyl.

20. A compound of claim 16, wherein $R^{1'}$ is $C_1$–$C_3$alkyl, and each of $R^{2'}$ and $R^{3'}$, independently of the other, is hydrogen, methyl or cyclopropyl, with the proviso that only one of the symbols $R^{2'}$ or $R^{3'}$ may be hydrogen.

21. Seeds of cultivated plants which have been treated with an antagonistically effective amount of a compound of formula I

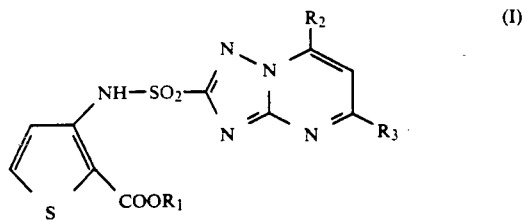

wherein $R^1$ is $C_1$–$C_6$alkyl or $C_3$–$C_6$cycloalkyl, and each of $R^2$ and $R^3$, independently of the other, is hydrogen, $C_1$–$C_3$alkyl, trifluoromethyl or cyclopropyl, with the proviso that only one of the symbols $R^2$ or $R^3$ may be hydrogen.

* * * * *